(12) United States Patent
Kolczewski et al.

(10) Patent No.: US 6,642,226 B2
(45) Date of Patent: Nov. 4, 2003

(54) SUBSTITUTED PHENYL-PIPERIDINE METHANONE COMPOUNDS

(75) Inventors: Sabine Kolczewski, Rheinfelden (DE); Stephan Roever, Inzlingen (DE); Patrick Schnider, Oberwil (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/057,450

(22) Filed: Jan. 25, 2002

(65) Prior Publication Data
US 2002/0151547 A1 Oct. 17, 2002

(30) Foreign Application Priority Data
Feb. 6, 2001 (EP) .............................. 01102557

(51) Int. Cl.$^7$ ...................... A61K 31/54; A61K 31/445; C07D 413/00; C07D 211/08; C07D 401/00
(52) U.S. Cl. .................. 514/227.8; 514/231.5; 514/235; 514/255; 514/256; 514/317; 514/318; 514/330; 514/331; 544/60; 546/194; 546/208
(58) Field of Search .................. 546/194, 208; 544/60, 129, 335, 360, 338; 514/227.8, 872, 318, 330, 331, 317, 231.5, 235.5, 255, 256

(56) References Cited

U.S. PATENT DOCUMENTS

| 5,972,938 A | 10/1999 | Rupniak et al. |
| 6,291,496 B1 | 9/2001 | Dannenberg et al. |
| 6,346,540 B1 * | 2/2002 | Janssens et al. ............ 514/326 |

FOREIGN PATENT DOCUMENTS

| CH | 545288 | 1/1974 |
| WO | WO 95/16679 | 6/1995 |
| WO | WO 95/18124 | 7/1995 |
| WO | WO 95/23798 | 9/1995 |
| WO | WO 97/25322 | 7/1997 |
| WO | WO 00/53572 | 9/2000 |

OTHER PUBLICATIONS

E.M. Kudlacz et al., "The peripheral NK–1/NK–2 receptor antagonist MDL 105, 172A inhibits tachykinin–mediated respiratory effects in guinea–pigs", *J. Auto. Pharmacology*, vol. 17, pp 109–119 (1997).

S. J. Veenstra et al., "*SAR OF 2–Benzyl–4–Aminopiperidines NK1 Antagonists. Synthesis of CGP 49823*", Biorganic & Med. Chem. Letters, vol. 6(24), pp. 3029–3034 (1996).

C. F. Koelssch, "*A Synthesis of 3–Phenylpiperdines*", J. Amer. Chem. Soc., vol. 65, pp. 2093–2095 (1943).

Doi et al., Eur. J. Pharmacol., 383, pp. 297–303 (1999).

Navari et al., The New England Journal of Medicine, 340, pp. 190–195 (1999).

Quartara et al., Neuropeptides, 32, pp. 1–49 (1998).

Maggi et al., J. Auton. Pharmacol., 13, pp. 23–93 (1993).

Longmore et al., Can. J. Pharmacol., 75, pp. 612–621 (1997).

Kramer et al., Science, 281, pp. 1640–1645 (1998).

Barker, R., Neurosci. Res., 7, pp. 187–214 (1996).

Petit et al., Eur. J. Med. Chem., 26, pp. 19–32 (1991).

Old et al., J. Am. Chem.. Soc., 120, pp. 9722–9723 (1998).

Wolfe et al., J. Am. Chem. Soc., 118, pp. 7215–7216 (1996).

\* cited by examiner

*Primary Examiner*—Patricia L. Morris
*Assistant Examiner*—Raymond Covington
(74) *Attorney, Agent, or Firm*—George W. Johnston; Patricia S. Rocha-Tramaloni; Kimberly J. Prior

(57) ABSTRACT

The invention relates to compounds of the formula

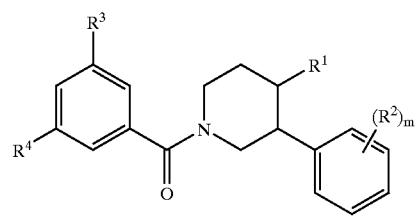

wherein $R^1$ is optionally substituted phenyl, morpholinyl, piperazinyl, pyrrolidinyl, piperidinyl or is thiomorpholinyl, 1-oxo-thiomorpholinyl or 1,1-dioxothiomorpholinyl. These compounds have a good affinity to the NK-1 receptor and they are therefore suitable in the control or treatment of diseases, related to this receptor.

25 Claims, No Drawings

SUBSTITUTED PHENYL-PIPERIDINE METHANONE COMPOUNDS

BACKGROUND

The neuropeptide receptor for substance P (NK-1) is widely distributed throughout the mammalian nervous system (especially brain and spinal ganglia), the circulatory system and peripheral tissues (especially the duodenum and jejunum) and is involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases is reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, The New England Journal of Medicine, Vol. 340, No. 3 190–195, 1999 describes the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

NK1 receptor antagonists have been reported to have also a beneficial effect in the therapy of traumatic brain injury (oral disclosure by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimmo, C. J. Bennett, X. Hu, I. Cernak, R. Vink)."

SUMMARY

The present invention is a compound of formula

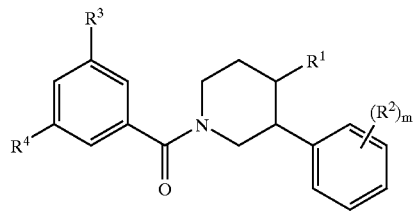

I wherein
$R^1$ a) is unsubstituted phenyl or phenyl substituted by at least one substituent selected from the group $R^{1'}$ consisting of halogen, trifluoromethyl, unsubstituted piperazinyl or piperazinyl substituted by lower alkyl, morpholinyl, NH-phenyl, pyrrolidinyl, $NH(CH_2)_n$—O-lower alkyl, $NR^aR^b$ $NH(CH_2)_n$-cycloalkyl and $NH(CH_2)_n$—$NR^cR^d$, or is b) unsubstituted morpholinyl, or morpholinyl substituted by one or two lower alkyl groups, or is c) unsubstituted piperazinyl, or piperazinyl substituted in the 4-position by the group $R^{1''}$ which is selected from the group consisting of lower alkyl, cycloalkyl, phenyl, benzoxazolyl, pyridinyl, pyrimidinyl pyrazinyl, $(CH_2)_n$-cycloalkyl, $(CH_2)_n$-phenyl, $(CH_2)_n$-hydroxy, $(CH_2)_n$—$CF_3$, $(CH_2)_n$—C(O)-morpholinyl, $(CH_2)_n$—C(O)—N($R^e$)-phenyl, wherein the phenyl ring is unsubstituted or substituted by a substitutent selected from the group consisting of lower alkyl, halogen and $(CH_2)_n$—C(O)—$NR^fR^g$, C(O)-phenyl, wherein the phenyl ring is unsubstituted or substituted by a substitutent selected from the group consisting of trifluoromethyl, C(O)—$(CH_2)_n$-phenyl, C(O)—$NR^hR^i$, C(O)—$NR^j$—$(CHR^k)_n$-phenyl, C(O)-lower alkyl,

C(O)—$CF_3$,

C(O)-cycloalkyl,
C(O)-morpholinyl,
C(O)O-lower alkyl,
C(O)—O—$(CH_2)_n$—$NR^lR^m$, and
$S(O)_2$-lower alkyl,
or is
d) unsubstituted pyrrolidinyl, or pyrrolidinyl substituted by at least one group $R^{1'''}$, selected from the group consisting of
halogen,
hydroxy,
=O,
$NR^nR^o$,
$N(cycloalkyl)_2$,
$N[(CH_2)_n cycloalkyl]_2$,
$NR^p$—C(O)-cycloalkyl, and
O—$(CH_2)_n$-cycloalkyl, or is
e) unsubstituted piperidinyl or piperidinyl substituted by at least one group $R^{1''''}$ in the 3 or 4-position, selected from the group consisting of
hydroxy,
=O,
halogen,
morpholinyl,
$NR^s$-cycloalkyl,
$NR^t$—C(O)-cycloalkyl,
$NR^u$—C(O)-phenyl,
$NR^v$—C(O)—$(CH_2)_n$-phenyl, and
O—$(CH_2)_n$-cycloalkyl,
or is
f) thiomorpholinyl, 1-oxo-thiomorpholinyl or 1,1-dioxothiomorpholinyl;
$R^2$ is independently selected from the group consisting of hydrogen, halogen, lower alkyl, —NH—$(CH_2)_n$—O-lower alkyl, pyrrolidinyl and morpholinyl;
$R^3/R^4$ are independently from each other trifluoromethyl or halogen;
$R^{a-v}$ are independently selected from the group consisting of hydrogen and lower alkyl;
n is 1, 2, 3 or 4;
m is 0, 1 or 2;
or a pharmaceutically acceptable acid addition salt thereof In more detail, the compounds of the present invention relate to the following formulae

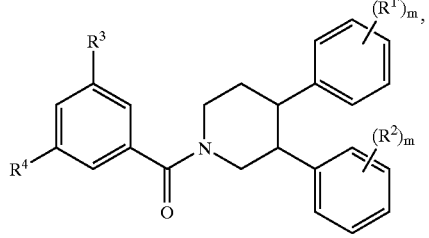

1A wherein m is 0, 1 or 2 and $R^{1'}$, $R^2$, $R^3$ and $R^4$ are described above, or to

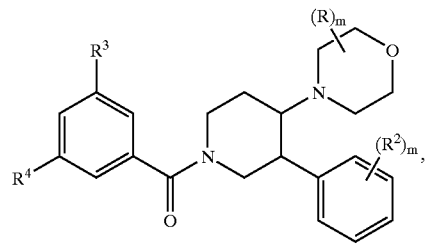

IB wherein R is lower alkyl, m is 0, 1 or 2, $R^2$, $R^3$ and $R^4$ have the significances given above, or to

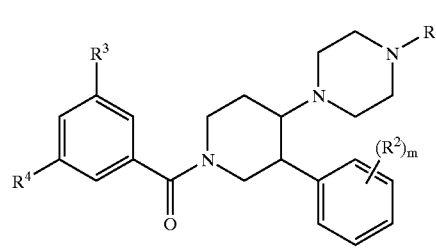

IC wherein m is 0, 1 or 2, $R^{1''}$, $R^2$, $R^3$ and $R^4$ have the significances given above, or to

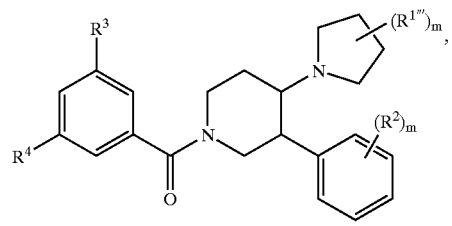

ID wherein m is 0, 1 or 2, $R^{1'''}$, $R^2$, $R^3$ and $R^4$ have the significances given above, or to

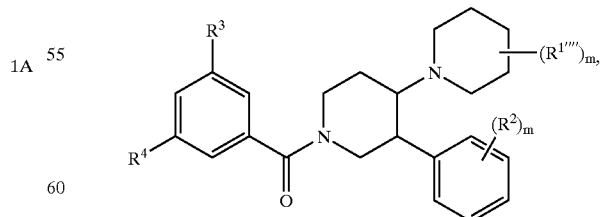

IE wherein m is 0, 1 or 2, $R^{1''''}$, $R^2$, $R^3$ and $R^4$ have the significances given above, or to

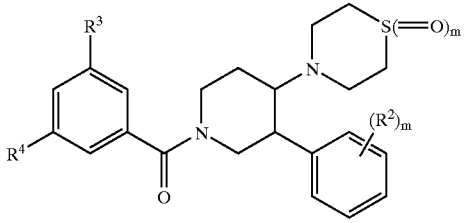

wherein $R^2$, $R^3$ and $R^4$ are described above and m is 0, 1 or 2.

Further encompassed by the present invention is a compound having the formula

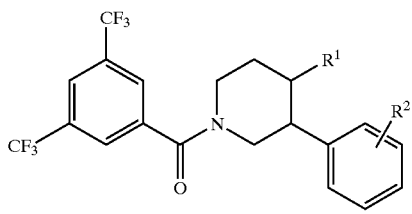

I-1 wherein
$R^1$ is unsubstituted phenyl, or phenyl substituted by one or two substituents, selected from the group $R^{1'}$, consisting of
halogen,
trifluoromethyl,
unsubstituted piperazinyl or piperazinyl substituted by lower alkyl,
morpholinyl,
NH-phenyl,
pyrrolidinyl,
$NH(CH_2)_n$—O-lower alkyl,
$NR^aR^b$,
$NH(CH_2)_n$-cycloalkyl, and —$NH(CH_2)_n$—$NR^cR^d$, or is
morpholinyl, or is
unsubstituted piperazinyl, or piperazinyl substituted by the group $R^{1''}$, which is selected from the group consisting of
lower alkyl,
cycloalkyl,
C(O)-phenyl, wherein the phenyl ring is optionally substituted by trifluoromethyl,
$(CH_2)_n$—C(O)—$NR^fR^g$,
$(CH_2)_n$-cycloalkyl,
$(CH_2)_n$-phenyl,
C(O)-lower alkyl,
C(O)—$CF_3$,
C(O)-cycloalkyl,
C(O)-morpholinyl,
C(O)—O—$(CH_2)_n$—$NR^lR^m$, and
$(CH_2)_n$—C(O)—$N(R^e)$-(unsubstituted) phenyl or —$(CH_2)_n$—C(O)—$N(R^e)$-phenyl substituted by
lower alkyl, or is
pyrazinyl, or is
unsubstituted pyrrolidinyl, or pyrrolidinyl substituted by the group $R^{1'''}$, which is selected from the group consisting of
hydroxy,
=O and
O—$(CH_2)_n$-cycloalkyl, or is
unsubsituted piperidinyl, or piperidinyl substituted by the group $R^{1''''}$, which is selected from the group consisting of
hydroxy,
O—$(CH_2)_n$-cycloalkyl,
=O and
halogen, or is
thiomorpholinyl, 1-oxo-thiomorpholinyl or 1,1-dioxothiomorpholinyl;
$R^2$ is selected from the group consisting of hydrogen, halogen, lower alkyl, —NH—$(CH_2)_n$—O-lower alkyl, pyrrolidinyl and morpholinyl;
$R^{a,b,c,d,e,f,g,l,m}$ is independently hydrogen or lower alkyl and n is 1, 2, 3 or 4;
or a pharmaceutically acceptable acid addition salt thereof.

The compound of formula I and pharmaceutically acceptable salts thereof are characterized by valuable therapeutic properties. It has been surprisingly found that the compounds of the present invention are antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The compound of formula I can also be used in form of a prodrug. Examples are esters, N-oxides, phosphate esters, glycoamide esters, glyceride conjugates and the like. The prodrugs may add improvements to the value of the present compound in adsorption, pharmacokinetics in distribution and transport to the brain.

The present invention is a compound of formula I or a pharmaceutically acceptable salt thereof, the preparation of the above-mentioned compounds, pharmaceutical compositions containing them and their manufacture as well as the use of the above-mentioned compounds in the control or prevention of illnesses, especially of illnesses and disorders of the kind referred to earlier or in the manufacture of corresponding pharmaceutical compositions.

The present invention includes all racemic compounds of formula I, also including corresponding enantiomers. Most of the enantiomers have been separated from their corresponding racemic compounds. It has been shown that certain individual enantiomers are more active in the test for NK-1 binding than racemic mixtures as described below. The preferred stereochemical position is the cis-position.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1–7 carbon atoms, for example, methyl, ethyl, propyl, isopropyl, n-butyl, i-butyl, t-butyl and the like.

Preferred lower alkyl groups are alkyl groups with 1–4 carbon atoms.

The term "lower alkoxy" denotes a group wherein the alkyl residues are as defined above, and which is attached via an oxygen atom to the structure.

The term "halogen" denotes chlorine, iodine, fluorine and bromine.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

Exemplary preferred are compounds of formula 1A, in which $R^{1'}$ is hydrogen, bromo, morpholinyl, 4-methyl-piperazinyl or —NH(CH$_2$)$_2$OCH$_3$, for example the following compounds:
rac-cis-(3,5-bis-trifluoromethyl-phenyl)-[4-(4-morpholin-4-yl-phenyl)-3-phenyl-piperidin-1-yl]-methanone,
rac-cis-(3,5-bis-trifluoromethyl-phenyl)-{4-[4-(4-methyl-piperazin-1-yl)-phenyl]-3-phenyl-piperidin-1-yl}-methanone,
rac-cis-(3,5-bis-trifluoromethyl-phenyl)-[3-(4-chloro-phenyl)-4-phenyl-piperidin-1-yl]-methanone,
rac-cis-(3,5-bis-trifluoromethyl-phenyl)-[4-(3-bromo-phenyl)-3-phenyl-piperidin-1-yl]-methanone or
rac-cis-(3,5-bis-trifluoromethyl-phenyl)-{4-[4-(2-methoxy-ethylamino)-phenyl]-3-phenyl-piperidin-1-yl}-methanone.

Further preferred are compounds of formula IB, wherein $R^2$ is hydrogen, fluoro or chloro. Examples of such compounds are:
rac-cis-(3,5-bis-trifluoromethyl-phenyl)-[3-(4-chloro-phenyl)-4-morpholin-4-yl-piperidin-1-yl]-methanone,
rac-cis-(3,5-bis-trifluoromethyl-phenyl)-(4-morpholin-4-yl-3-phenyl-piperidin-1-yl)-methanone,
rac-cis-(3,5-bis-trifluoromethyl-phenyl)-[3-(4-fluoro-phenyl)-4-morpholin-4-yl-piperidin-1-yl]-methanone or
Rac-cis-(3,5-bis-trifluoromethyl-phenyl)-[3'-(4-chloro-phenyl)-4-morpholin-4-yl-[1,4']bipiperidinyl-1'-yl]-methanone.

Further preferred are compounds of formula IC, wherein $R^{1''}$ is hydrogen, methyl, —C(O)CF$_3$, —(CH$_2$)$_2$OH, —CH$_2$C(O)N(CH$_3$)$_2$, CH$_2$-cyclopropyl, benzyl, —C(O)-cyclopropyl, —C(O)-morpholinyl, pyrazinyl, cyclopropyl or —CH$_2$CONHC$_6$H$_3$(CH$_3$)$_2$, —CH$_2$CONHC$_6$H$_4$F, —C(O)CH$_2$-phenyl, and R$_2$ is hydrogen, methyl, chloro or fluoro.
Examples of such compounds are:
rac-cis-(3,5-bis-trifluoromethyl-phenyl)-[4-(4-methyl-piperazin-1-yl), -3-phenyl-piperidin-1-yl]-methanone,
rac-cis-(3,5-bis-trifluoromethyl-phenyl)-(3-phenyl-4-piperazin-1-yl-piperidin-1-yl)-methanone,
rac-cis-2{4-[1-(3,5-bis-trifluoromethyl-benzoyl)-3-phenyl-piperidin-4-yl]-piperazin-1-yl}-N,N-dimethyl-acetamide,
rac-cis-(3,5-bis-trifluoromethyl-phenyl)-[4-(4-cyclopropylmethyl-piperazin-1-yl)-3-phenyl-piperidin-1-yl]-methanone,
rac-cis-[4-(4-benzyl-piperazin-1-yl)-3-phenyl-piperidin-1-yl]-(3,5-bis-trifluoromethyl-phenyl)-methanone,
rac-cis-(3,5-bis-trifluoromethyl-phenyl)-[4-(4-cyclopropanecarbonyl-piperazin-1-yl)-3-phenyl-piperidin-1-yl]-methanone,
rac-cis-{4-[1-(3,5-bis-trifluoromethyl-benzoyl)-3-phenyl-piperidin-4-yl]-piperazin-1-yl}-morpholin-4-yl-methanone,
rac-cis-(3,5-bis-trifluoromethyl-phenyl)-[4-(4-cyclopropyl-piperazin-1-yl)-3-phenyl-piperidin-1-yl]-methanone,
rac-cis-(3,5-bis-trifluoromethyl-phenyl)-[3-(4-fluoro-phenyl)-4-(4-methyl-piperazin-1-yl)-piperidin-1-yl]-methanone,
rac-cis-2-{4-[1-(3,5-bis-trifluoromethyl-benzoyl)-3-phenyl-piperidin-4-yl]-piperazin-1-yl}-N-(2,6-dimethyl-phenyl)-acetamide,
rac-cis-(3,5-bis-trifluoromethyl-phenyl)-[3-phenyl-4-(2,3,5,6-tetrahydro-[1,2']bipyrazinyl-4-yl)-piperidin-1-yl]-methanone,
(+)-(3,5-bis-trifluoromethyl-phenyl)-[4-(4-cyclopropanecarbonyl-piperazin-1-yl)-3-phenyl-piperidin-1-yl]-methanone,
Rac-cis-2-{4-[1-(3,5-bis-trifluoromethyl-benzoyl)-3-phenyl-piperidin-4-yl]-piperazin-1-yl}-N-(4-fluoro-phenyl)-acetamide,
Rac-cis-1-{4-[1-(3,5-bis-trifluoromethyl-benzoyl)-3-phenyl-piperidin-4-yl]-piperazin-1-yl}-2-phenyl-ethanone,
Rac-cis-(3,5-bis-trifluoromethyl-phenyl)-[3-(4-fluoro-phenyl)-4-piperazin-1-yl-piperidin-1-yl]-methanone,
Rac-cis-(3,5-bis-trifluoromethyl-phenyl)-[4-(4-cyclopropylmethyl-piperazin-1-yl)-3-(4-fluoro-phenyl)-piperidin-1-yl]-methanone,
(−)-(3,5-bis-trifluoromethyl-phenyl)-[3-(4-fluoro-phenyl)-4-(4-methyl-piperazin-1-yl)-piperidin-1-yl]-methanone,
(−)-(3,5-bis-trifluoromethyl-phenyl)-[3-phenyl-4-(4-methyl-piperazin-1-yl)-piperidin-1-yl]-methanone,
(−)-4-(3,5-bis-trifluoromethyl-phenyl)-[4-(4-cyclopropylmethyl-piperazin-1-yl)-3-p-tolyl-piperidin-1-yl]-methanone,
(−)-(3,5-bis-trifluoromethyl-phenyl)-[4-(4-cyclopropanecarbonyl-piperazin-1-yl)-3-p-tolyl-piperidin-1-yl]-methanone,
(−)-(3,5-bis-trifluoromethyl-phenyl)-{4-[4-(morpholine-4-carbonyl)-piperazin-1-yl]-3-p-tolyl-piperidin-1-yl}-methanone,
Rac-cis-1-{4-[1-(3,5-bis-trifluoromethyl-benzoyl)-3-(4-chloro-phenyl)-piperidin-4-yl]-piperazin-1-yl}-2,2,2-trifluoro-ethanone,
(−)-1-{4-[1-(3,5-bis-trifluoromethyl-benzoyl)-3-(4-chloro-phenyl)-piperidin-4-yl]-piperazin-1-yl}-2,2,2-trifluoro-ethanone,
(−)-(3,5-bis-trifluoromethyl-phenyl)-[4-(4-cyclopropyl-piperazin-1-yl)-3-p-tolyl-piperidin-1-yl]-methanone,
(−)-(3,5-bis-trifluoromethyl-phenyl)-[4-(4-methyl-piperazin-1-yl)-3-p-tolyl-piperidin-1-yl]-methanone,
(−)-(3,5-bis-trifluoromethyl-phenyl)-[3-(4-chloro-phenyl)-4-(4-cyclopropylmethyl-piperazin-1-yl)-piperidin-1-yl]-methanone,
(−)-(3,5-bis-trifluoromethyl-phenyl)-[4-(4-cyclopropylmethyl-piperazin-1-yl)-3-phenyl-piperidin-1-yl]-methanone,
(−)-(3,5-bis-trifluoromethyl-phenyl)-{4-[4-(2-hydroxy-ethyl)-piperazin-1-yl]-3-phenyl-piperidin-1-yl}-methanone or
(−)-(3,5-bis-trifluoromethyl-phenyl)-[4-(4-cyclopropyl-piperazin-1-yl)-3-phenyl-piperidin-1-yl]-methanone.

Further preferred are compounds of formula IE, wherein $R^{1'''}$ is selected from the group consisting of fluoro, hydroxy, —NHC(O)-cyclopropyl, —NHC(O)CH$_2$-phenyl, —NH-cyclopropyl, —N(CH$_2$)$_2$, —OCH$_2$-cyclopropyl and =O and R$^2$ is hydrogen, chloro or fluoro. Examples of such compounds are:
rac-cis-(3,5-bis-trifluoromethyl-phenyl)-(4,4-difluoro-3'-phenyl-[1,4']bipiperidinyl-1'-yl)-methanone,
rac-cis-(3,5-bis-trifluoromethyl-phenyl)-[3'-(4-fluoro-phenyl)-3-hydroxy-[1,4']bipiperidinyl-1'-yl]-methanone,
rac-cis-(3,5-bis-trifluoromethyl-phenyl)-(4-hydroxy-3'-phenyl-[1,4'] bipiperidinyl-1'-yl)-methanone,
rac-cis-(3,5-bis-trifluoromethyl-phenyl)-(4-cyclopropylmethoxy-3'-phenyl-[1,4']bipiperidinyl-1'-yl)-methanone, rac-cis-1'-(3,5-bis-trifluoromethyl-benzoyl)-3'-phenyl-[1,4']
bipiperidinyl-4-one,
Rac-cis-(3,5-bis-trifluoromethyl-phenyl)-[3'-(4-chloro-
phenyl)-4-hydroxy-[1,4']bipiperidinyl-1'-yl]-methanone,
Rac-cis-(3,5-bis-trifluoromethyl-phenyl)-[3'-(4-chloro-
phenyl)-4-cyclopropylmethoxy-[1,4']bipiperidinyl-1'-yl]-
methanone,
(3RS,3'RS,4SR)- and (3RS,3'SR,4SR)-
cyclopropanecarboxylic acid [1'-(3,5-bis-trifluoromethyl-
benzoyl)-3'-(4-fluoro-phenyl)-[1,4']bipiperidinyl-3-yl]-
amide,
(3RS,3'RS,4SR)- and (3RS,3'SR,4SR)-N-[1'-(3,5-bis-
trifluoromethyl-benzoyl)-3'-(4-fluoro-phenyl)-[1,4']
bipiperidinyl-3-yl]-2-phenyl-acetamide,
Rac-cis-(3,5-bis-trifluoromethyl-phenyl)-[3'-(4-chloro-
phenyl)-4-dimethylamino-[1,4']bipiperidinyl-1'-yl]-
methanone or
Rac-cis-(3,5-bis-trifluoromethyl-phenyl)-[3'-(4-chloro-
phenyl)-4-cyclopropylamino-[1,4']bipiperidinyl-1'-yl]-
methanone.

Further preferred are compounds of formula ID, wherein R$^{1'''}$ is selected from the group consisting of hydrogen, hydroxy,
amino, —OCH$_2$-cyclopropyl and =O and R$^2$ is hydrogen, chloro or fluoro. Examples of such compounds are:
(3R,3'R,4R)- and (3S,3'R,4S)-(3,5-bis-trifluoromethyl-
phenyl)-[4-(3'-hydroxy-pyrrolidin-1'-yl)-3-phenyl-
piperidin-1-yl]-methanone,
(3R,3'R,4R)- and (3S,3'R,4S)-(3,5-bis-trifluoromethyl-
phenyl)-[4-(3-cyclopropylmethoxy-pyrrolidin-1-yl)-3-
phenyl-piperidin-1-yl]-methanone,
rac-cis-1-[1-(3,5-bis-trifluoromethyl-benzoyl)-3-phenyl-
piperidin-4-yl]-pyrrolidin-3-one,
(−)-(3,5-bis-trifluoromethyl-phenyl)-[3-(4-chloro-phenyl)-
4-pyrrolidin-1-yl-piperidin-1-yl]-methanone or
(3RS,3'RS,4SR)- and (3RS,3'SR,4SR)-[4-(3-amino-
pyrrolidin-1-yl)-3-(4-fluoro-phenyl)-piperidin-1-yl]-(3,5-
bis-trifluoromethyl-phenyl)-methanone.

Further preferred are compounds of formula IF, wherein m is 0, 1 or 2 and R$^2$ is hydrogen. Examples of such compounds are:
rac-cis-(3,5-bis-trifluoromethyl-phenyl)-(3-phenyl-4-
thiomorpholin-4-yl-piperidin-1-yl)-methanone,
rac-cis-(3,5-bis-trifluoromethyl-phenyl)-[4-(1-oxo-1l
4-thiomorpholin-4-yl)-3-phenyl-piperidin-1-yl]-
methanone or
rac-cis-(3,5-bis-trifluoromethyl-phenyl)-[4-(1,1-dioxo-1l
6-thiomorpholin-4-yl)-3-phenyl-piperidin-1-yl]-
methanone.

The present compounds of formula I and their pharmaceutically acceptable salts can be prepared by methods known in the art, for example, by processes described below, which process comprises
reacting a compound of formula

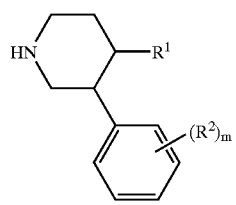

II with a compound of formula

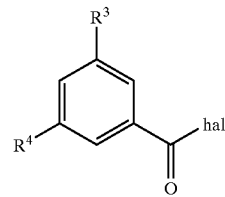

III forming a compound of formula

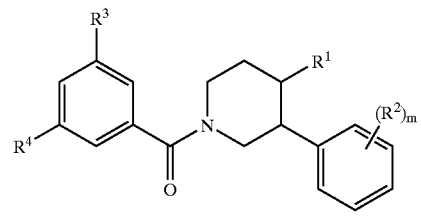

I wherein R$^1$ is unsubstituted phenyl, or phenyl substituted by halogen, R$^2$, R$^3$ and R$^4$ have the significances given above, hal is halogen and m is 0, 1 or 2,
or
reacting a compound of formula

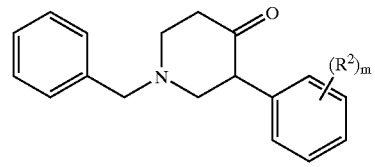

IV with a compound selected from the group of formulae

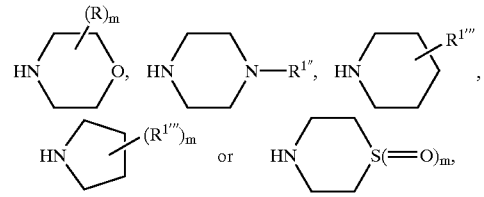

debenzylating, and then acylating with a compound of formula III forming give a compound of formulae

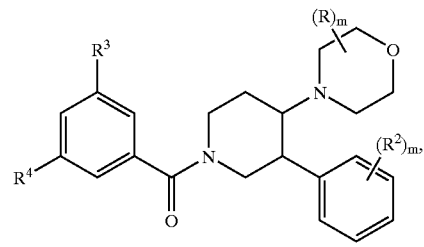

IB wherein R, R$^2$, R$^3$, R$^4$ and m have the significances given above, or

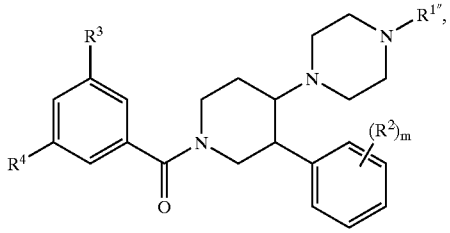

IC wherein $R^{1''}$, $R^2$, $R^3$, $R^4$ and m have the significances given above, or

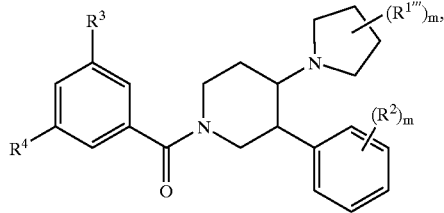

ID wherein $R^{1'''}$, $R^2$, $R^3$, $R^4$ and m have the significances given above, or

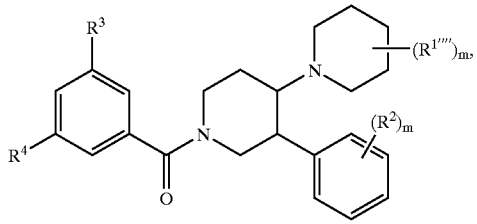

IE wherein $R^{1''''}$, $R^2$, $R^3$, $R^4$ and m have the significances given above, or

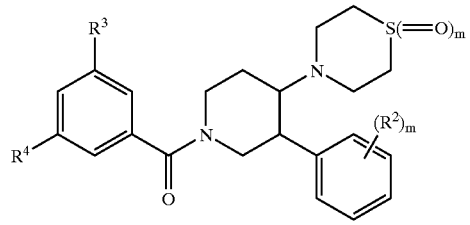

IF wherein $R^2$, $R^3$, $R^4$ and m have the significances given above, or aminating a compound of formula

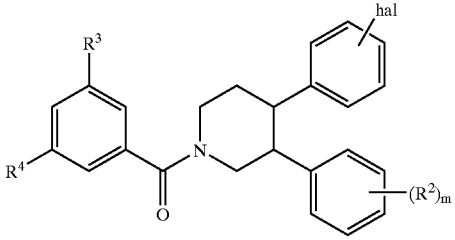

V with an amine derivative of formula $R^1H$  VI forming a compound of formula

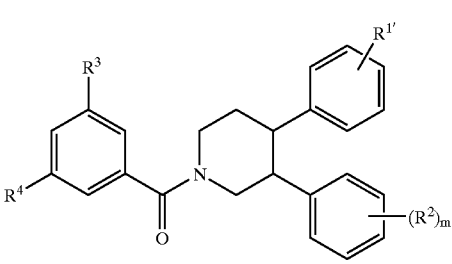

IA1 wherein $R^{1'}$ is piperazinyl, optionally substituted by lower alkyl, morpholinyl, —NH-phenyl, pyrrolidinyl, —NH(CH$_2$)$_n$—O-lower alkyl, —NR$^f$R$^g$, —NH(CH$_2$)$_n$-cycloalkyl or —NH(CH$_2$)$_n$-NR$^c$R$^d$, and the definitions of $R^2$, $R^3$ and $R^4$ are given above, or eacting a compound of formula

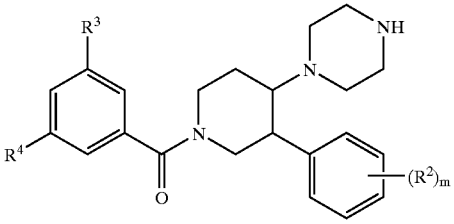

IC1 with a compound of formula $R^{1''}hal$  VII forming a compound of formula

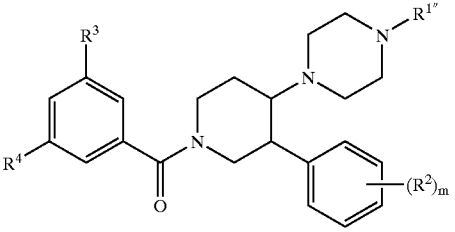

IC wherein the definitions of substituents are given above, or oxidizing a compound of formula oxidizing a compound of formula

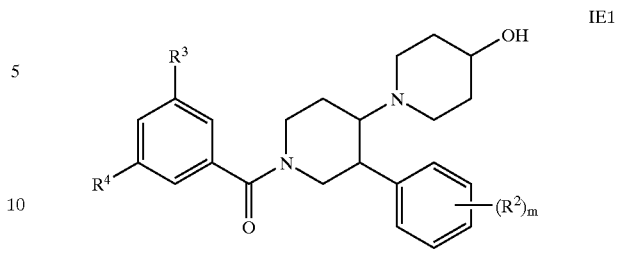

IF1

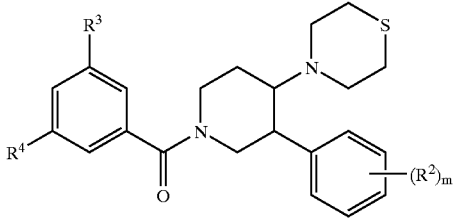

to a compound of formula

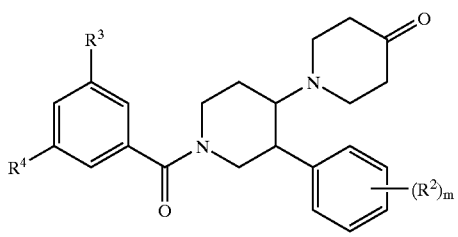

IE3 with Oxone® forming a compound of formula

IF

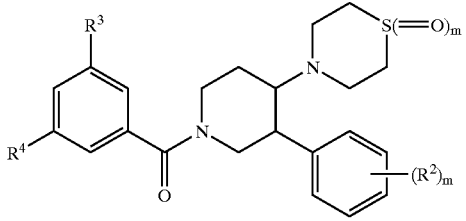

wherein $R^2$, $R^3$, $R^4$ and m are described above, or halogenating a compound of formula

IE3 wherein m is 1 or 2 and $R^2$, $R^3$ and $R^4$ are described above, or alkylating a compound of formula

IE1

[Structure IE3 repeated]

forming a compound of formula

IE4

[Structure IE4 with hal groups]

with a compound of formula $R^5$hal  VIII to a compound of formula

IE2

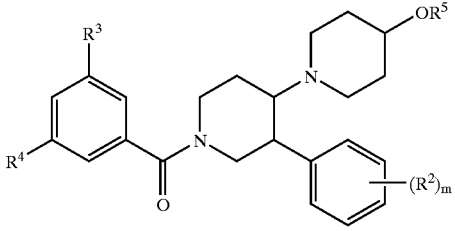

and if desired, converting the compound obtained into a pharmaceutically acceptable acid addition salt.

The following schemes 1–8 and specific examples 1 to 130 describe the processes for preparation of compounds of formula I in more detail. The starting materials are known compounds and were prepared according to methods known in the art.

wherein $R^5$ is —$(CH_2)_n$-cycloalkyl) and $R^2$, $R^3$, $R^4$ and m are described above, or or Scheme 1

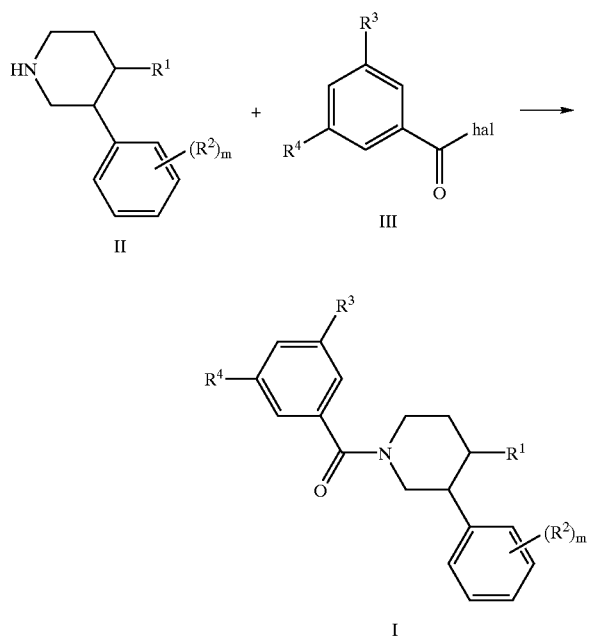

R[1] is phenyl, optionally substituted by halogen) R[2], R[3] and R[4] are described above, m is 0, 1 or 2 and hal is chloro or bromo.

Starting materials of formula II or their salts are obtained according to known procedures (e.g. Petit, S.; Nallet, J. P.; Guillard, M.; Dreux, J.; Chermat, R.; Poncelet, M.; Bulach, C.; Simon, P.; Fontaine, C.; et al, Eur. *J. Med. Chem.* 1991, 26, 19–32).

Compounds of formula I are obtained by acylation of a compound of formula II with an acid chloride of formula III in the presence of a base, like triethylamine, in an inert solvent like methylene chloride.

Scheme 2

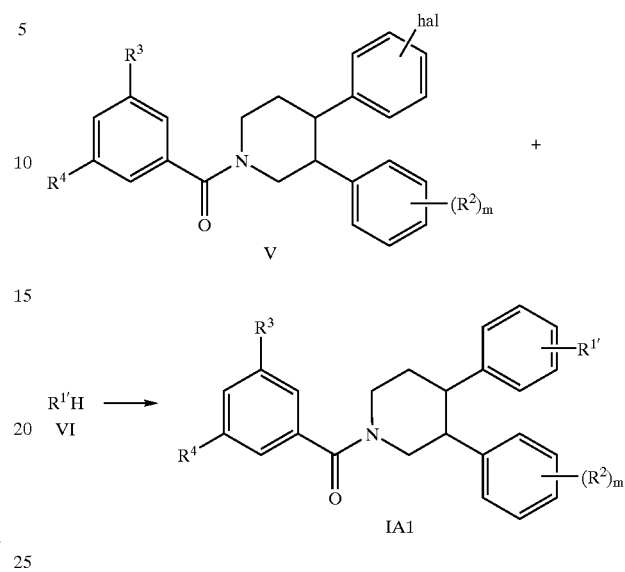

R[2] is described above, m is 0, 1 or 2 and R[1'] is piperazinyl, or piperazinyl substituted by lower alkyl, or is morpholinyl, —NH-phenyl, pyrrolidinyl, —NH(CH$_2$)$_n$-O-lower alkyl, —NR$^a$R$^b$, —NH(CH$_2$)$_n$-cycloalkyl or —NH(CH$_2$)$_n$-NR$^c$R$^d$. Hal is bromo or chloro and m is 0, 1 or 2.

Compounds of formula 1A1 can be obtained by amination of aromatic chlorides or bromides of formula V using an amine of formula VI, like morpholine or N-methylpiperazine, and sodium tert-butoxide, a catalyst like tris(dibenzylideneacetone)dipalladium(O) and a ligand like rac-2,2'-bis(diphenylphosphino)-1,1'-binaphthyl or biphenyl-2-yl-dicyclohexyl-phosphane in an inert solvent like toluene. The method is described in detail in S. Buchwald et al, *J. Am. Chem. Soc.* 1996, 118, 7215–7218 and *J. Am. Chem. Soc.* 1998, 120, 9722–9723.

Scheme 3

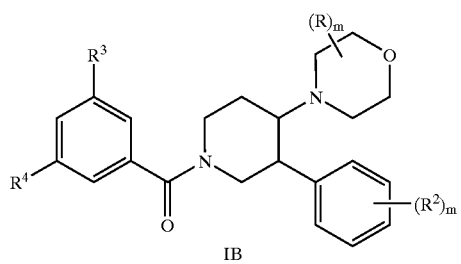

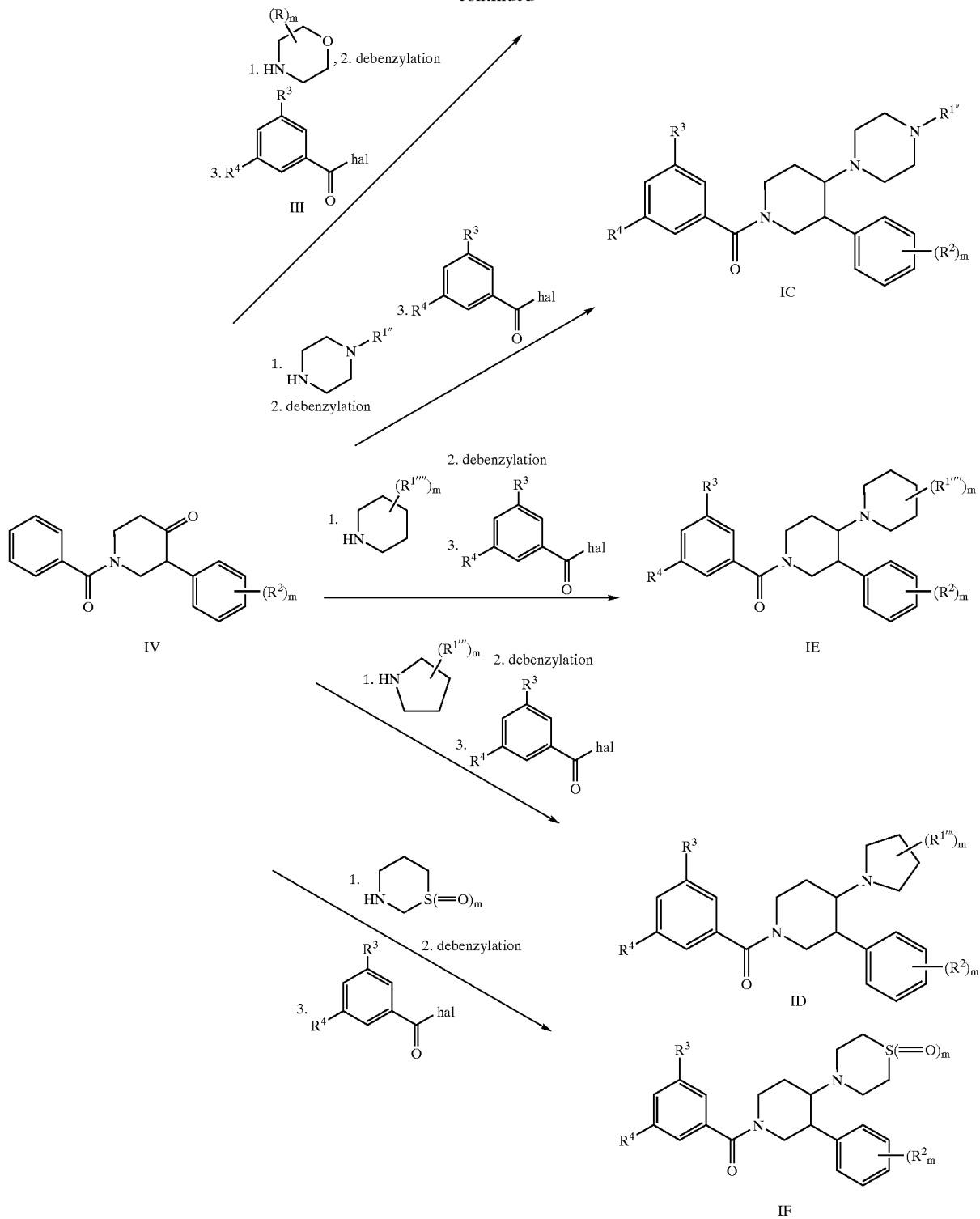

Starting materials of formula IV are obtained according to literature procedures (e.g. Lindenmann, Adolf; Suess, Rudolf., CH 545288.)

Compounds of formula IB, IC, ID, IE and IF are obtained by the following sequence of reactions:
1. Reductive amination of a ketone of formula IV using the cyclic tertiary amine as described in scheme 3, an activating agent like titanium(IV)isopropoxide and a reducing agent, like sodium cyanoborohydride, in a protic solvent like methanol or ethanol, followed by hydrolysis of the intermediate cyanamide, using sodium hydroxide in ethylenglycol for the preparation of compounds of formula IC1.

2. Protection of the hydrogen atom on the cyclic amine using trifluoroacetic acid anhydride, 4-dimethylaminopyridine and pyridine in methylene chloride (only for the preparation of compounds of formula IC1).
3. Debenzylation with catalytic amounts of 10% Pd/C with hydrogen at 1 atm in methanol at acidic pH, or debenzylation using 1-chloroethyl chloroformate in methylene chloride followed by refluxing in methanol.
4. Acylation with an acid chloride of formula III in the presence of a base like triethylamine in an inert solvent like methylene chloride.
5. Deprotection of the trifluoroacetamide using potassium carbonate in a mixture of methanol and water (for the preparation of compounds of formula IC1 only).

Scheme 4

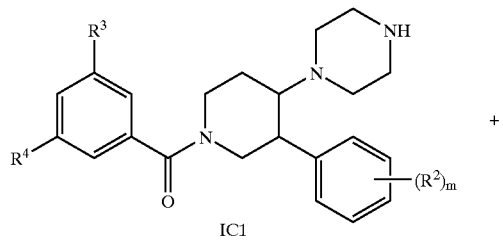

IC1

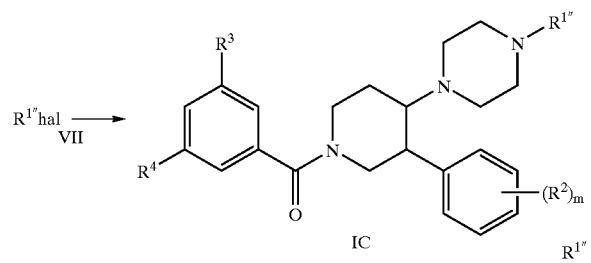

IC $R^2$, $R^3$ and $R^4$ and m have the significances given above and hal is chloro or bromo.

Compounds of formula IC are obtained by
alkylating a compound of formula IC1 with an alkyl chloride or alkyl bromide of formula VII in an inert solvent like N,N-dimethylforamide in the presence of a base like potassium carbonate, or
acylating a compound of formula IC1 with an acid chloride of formula $R^{1''}$ in an inert solvent like methylene chloride in the presence of a base like triethyl amine, or
treating a compound of formula IC1 with an aromatic bromide or chloride of formula VII at an elavated temperature without any solvent.

Scheme 5

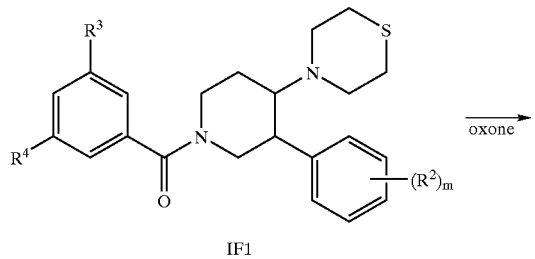

IF1

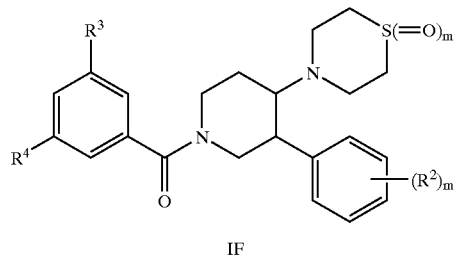

IF $R^2$, $R^3$ and $R^4$ have the significances given above and m is 1 or 2.

Sulfoxides of formula IF (m=1) are obtained by treating a thiomorpholine of formula IF1 with 0.6 eq of potassium peroxymonosulfate (Oxone®, available from E. I. duPont, Wilmington, Del.).

Sulfones of formula IF (m=2) are obtained by treating a thiomorpholine of formula IF1 with an excess of potassium peroxymonosulfate (Oxone®).

Scheme 6

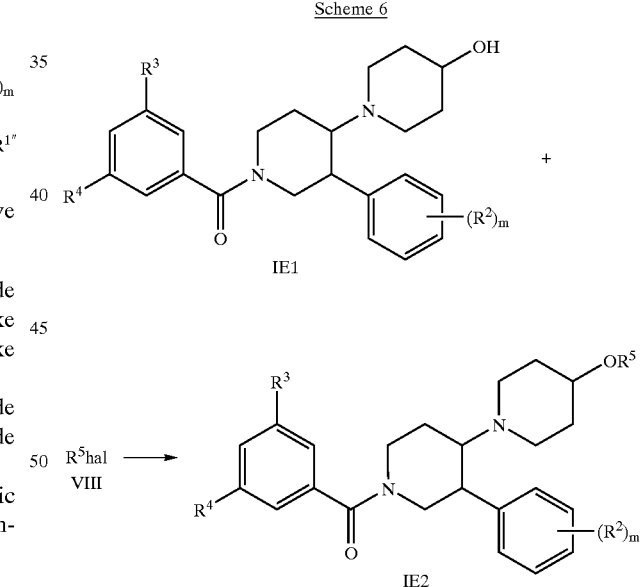

$R^2$, $R^3$ and $R^4$ have the significances given above and $R^5$ may be, for example, —$(CH_2)_n$-cycloalkyl. Hal is chloro or bromo.

Ethers of formula IE2 are obtained by treating an alcohol of formula IE1 with a base like sodium hydride and an alkylating agent like an alkyl bromide or alkyl chloride of formula VIII in an inert solvent like dimethylformamide.

Scheme 7

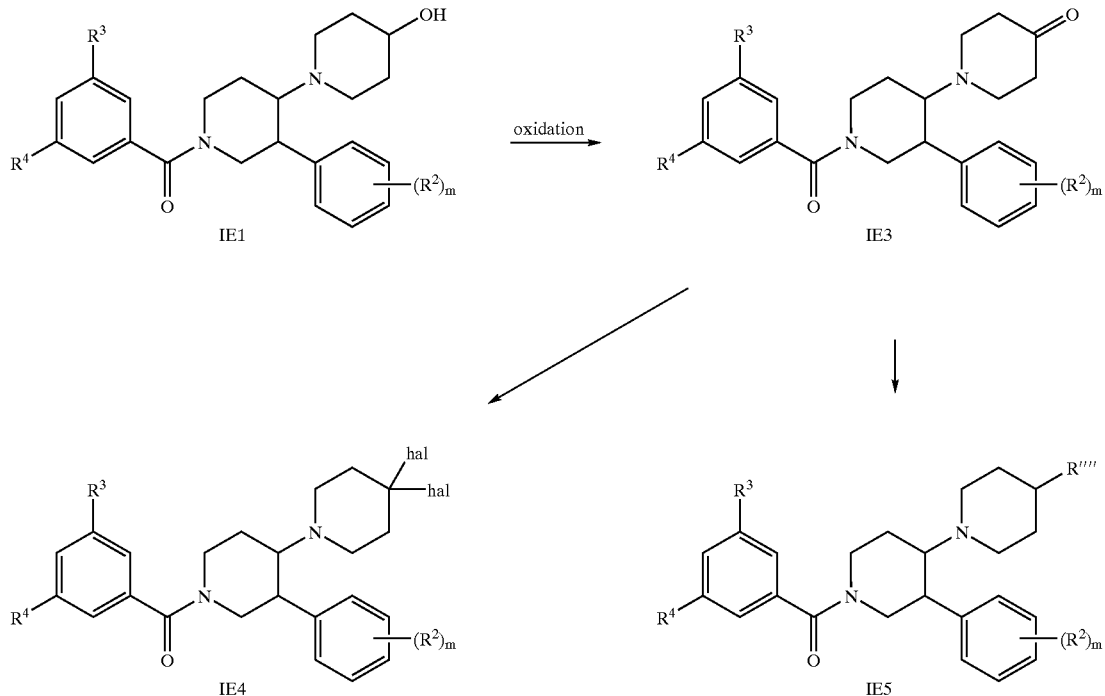

R"" is morpholinyl, —NR"R°, —NR$^p$-cycloalkyl, —NR—C(O)-cycloalkyl, —NR$^q$—C(O)-phenyl or —NR$^r$—C(O)—(CH$_2$)$_n$-phenyl, R$^{n,o,p,q,r}$, R$^2$, R$^3$, R$^4$ and m have the significances given above and hal is preferably fluoro.

Ketone derivatives of formula IE3 are obtained by Swern oxidation of an alcohol of formula IE1 by methods known in the art.

Compounds of formula IE4 are obtained by treating a ketone of formula IE3 with, for example, diethylamino sulfurtrifluoride, in an inert solvent like methylene chloride.

Compounds of formula IE5 are obtained by reductive amination by treating a ketone of formula IE3 with, for example, titanium(IV) isopropoxide and a mixture of ammonium chloride and triethylamine or a primary or secondary amine and consecutively with sodium borohydride or sodium cyanoborohydride or by substitution of an alcohol IE1 with the sequence (a) reaction with methanesulfonyl chloride and triethylamine in dichloromethane, (b) treatment with sodium azide in dimethylformamide (c), reduction of the intermediate azide with hydrogen and a palladium catalyst (d) alkylation or acylation of the free amine.

Scheme 8

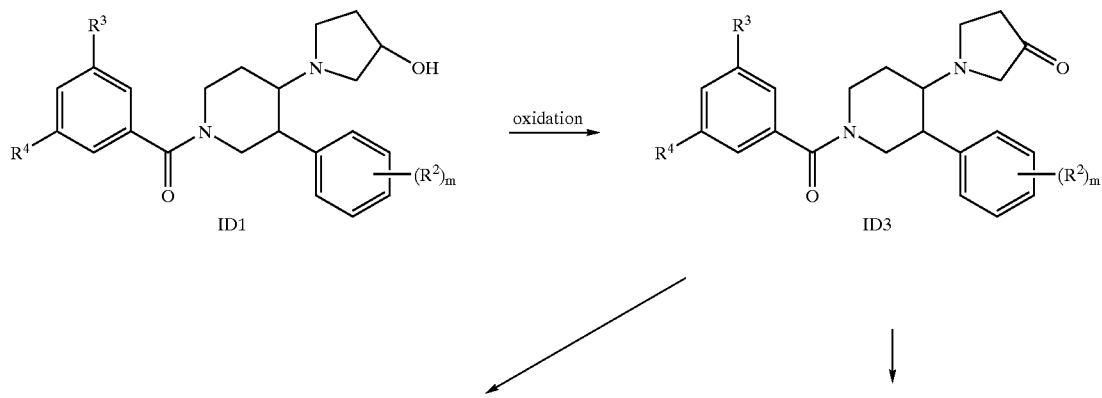

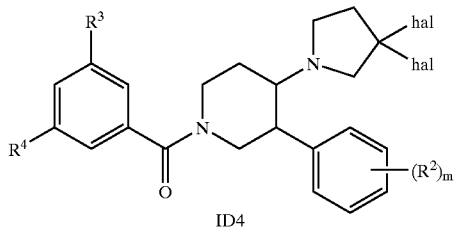

ID4

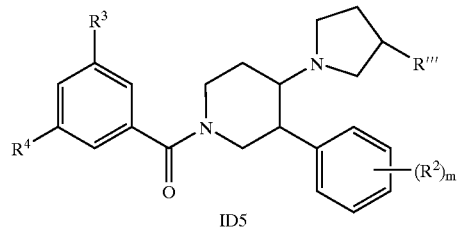

ID5

-continued

The preparation of compounds shown in scheme 8 is carried out in accordance with the preparation of compounds shown in scheme 7.

R'" is NR"R°, —N(cycloalkyl)$_2$, —N[(CH$_2$)$_n$-cycloalkyl]$_2$ or —NR$^p$—C(O)-cycloalkyl, R$^{n,o,p}$, R$^2$, R$^3$, R$^4$ and m have the significances given above and hal is preferably fluoro.

The salt formation is effected at room temperature in accordance with methods which are known and are familiar to any person skilled in the art. Not only salts with inorganic acids, but also salts with organic acids are formed by these methods. Hydrochlorides, hydrobromides, sulphates, nitrates, citrates, acetates, maleates, succinates, methanesulphonates, p-toluenesulphonates and the like are examples of such salts.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the NK$_1$ receptor was evaluated at human NK$_1$ receptors in CHO cells infected with the human NK$_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), MnCl$_2$ (3 mM) and phosphoramidon (2 μM). Binding assays consisted of 250 μl of membrane suspension (1.25×10$^5$ cells/assay tube), 0.125 μl of buffer of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 6.70–9.44 for the compounds of formula I of the present invention. The preferred compounds with a pKi>8.5 are shown in table I below:

TABLE I

| Example No. | pKi | Example No. | pKi |
|---|---|---|---|
| 27 | 8.51 | 103 | 8.67 |
| 36 | 8.90 | 104 | 8.63 |
| 63 | 8.67 | 106 | 8.50 |
| 65 | 8.85 | 107 | 9.20 |
| 66 | 8.56 | 108 | 8.89 |

TABLE I-continued

| Example No. | pKi | Example No. | pKi |
|---|---|---|---|
| 70 | 8.59 | 109 | 8.79 |
| 77 | 8.53 | 110 | 8.98 |
| 79 | 8.69 | 111 | 9.34 |
| 80 | 8.50 | 112 | 9.10 |
| 82 | 8.68 | 113 | 9.44 |
| 88 | 8.50 | 114 | 9.44 |
| 90 | 8.61 | 115 | 9.04 |
| 92 | 8.57 | 118 | 8.75 |
| 102 | 9.28 | 119 | 9.00 |

Furthermore, it has been shown that the compounds of formula I have a good water-solubility as shown in table II below. This advantage of compounds of formula I over other NK-1-related compounds extends the practicability in administration with regard to certain forms of application.

TABLE II

| | Solubility at pH 6.5 [mg/mL] | Solubility at pH 4.3 [mg/mL] |
|---|---|---|
| Example 27 | 0.91 | >8.4 |
| Example 34 | | >3.5 |
| Example 36 | | >7.5 |
| Example 45 | 1.0 | 2.4 |
| Example 63 | 0.78 | 1.0 |
| Example 102 | 0.43 | 5.5 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc can be used as such excipients e.g. for tablets, dragees and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. Unless indicated otherwise, all of the compounds were prepared and characterized by the given methods. All temperatures are given in degrees Celsius.

EXAMPLE 1

Rac-cis-(3,5-Bis-trifluoromethyl-phenyl)-[4-(3,4-dichloro-phenyl)-3-phenyl-piperidin-1-yl]-methanone To a suspension of rac-cis-4-(3,4-dichlorophenyl)-3-phenyl-piperidine hydrochloride (200 mg, 0.58 mmol) in 20 mL dichloromethane was added triethylamine (0.35 mL, 2.5 mmol) and 3,5-bistrifluoromethyl-benzoyl chloride (0.11 mL, 0.60 mmol). The reaction mixture was stirred at room temperature overnight and then diluted with 20 mL water. The organic phase was separated and the aqueous layer was extracted twice with 20 mL dichloromethane. Organic phases were pooled, dried with magnesium sulfate and evaporated. Recrystallization of the crude product from diisopropylether and hexanes gave the desired product (268 mg, 84%) as white crystals, MS: m/e=546.1 ($M^+$).

EXAMPLE 2

Rac-cis-(3,5-Bis-trifluoromethyl-phenyl)-(3,4-diphenyl-piperidin-1-yl)-methanone The title compound, MS: m/e=478.2 ($M+H^+$), was prepared in accordance with the general method of example 1 from 3,5-bis(trifluoromethyl)benzoyl chloride and rac-cis-3,4-diphenylpiperidine.

EXAMPLE 3

Rac-cis-(3,5-Bis-trifluoromethyl-phenyl)-[4-(2-chloro-phenyl)-3-phenyl-piperidin-1-yl]-methanone The title compound, MS: m/e=512.2 ($M^+$), was prepared in accordance with the general method of example 1 from 3,5-bis(trifluoromethyl)benzoyl chloride and rac-cis-4-(o-chlorophenyl)-3-phenylpyridine hydrochloride.

EXAMPLE 4

Rac-cis-(3,5-Bis-trifluoromethyl-phenyl)-[3-phenyl-4-(3-trifluoromethyl-phenyl)-piperidin-1-yl]-methanone The title compound, MS: m/e=546.1 ($M+H^+$), was prepared in accordance with the general method of example 1 from 3,5-bis(trifluoromethyl)benzoyl chloride and rac-cis-3-phenyl-4-(3-trifluoromethylphenyl)piperidine hydrochloride.

EXAMPLE 5

Rac-cis-(3,5-Bis-trifluoromethyl-phenyl)-[3-(2-chloro-phenyl)-4-phenyl-piperidin-1-yl]-methanone The title compound, MS: m/e=512.2 ($M^+$), was prepared in accordance with the general method of example 1 from 3,5-bis(trifluoromethyl)benzoyl chloride and rac-cis-3-(2-chloro-phenyl)-4-phenyl-piperidine hydrochloride.

EXAMPLE 6

Rac-cis-(3,5-Bis-trifluoromethyl-phenyl)-[3-(3-chloro-phenyl)-4-phenyl-piperidin-1-yl]-methanone The title compound, MS: m/e=512.2 ($M^+$), was prepared in accordance with the general method of example 1 from 3,5-bis(trifluoromethyl)benzoyl chloride and rac-cis-3-(3-chloro-phenyl)-4-phenyl-piperidine hydrochloride.

EXAMPLE 7

Rac-cis-(3,5-Bis-trifluoromethyl-phenyl)-[4-(3-bromo-phenyl)-3-phenyl-piperidin-1-yl]-methanone The title compound, MS: m/e=556.0 ($M^+$), was prepared in accordance with the general method of example 1 from 3,5-bis(trifluoromethyl)benzoyl chloride and rac-cis-4-(3-bromo-phenyl)-3-phenyl-piperidine hydrochloride.

EXAMPLE 8

Rac-cis-(3,5-Bis-trifluoromethyl-phenyl)-[4-(4-chloro-phenyl)-3-phenyl-piperidin-1-yl]-methanone The title compound, MS: m/e=512.2 ($M^+$), was prepared in accordance with the general method of example 1 from 3,5-bis(trifluoromethyl)benzoyl chloride and rac-cis-4-(4-chloro-phenyl)-3-phenyl-piperidine hydrochloride.

EXAMPLE 9

Rac-cis-(3,5-Bis-trifluoromethyl-phenyl)-[3-(4-chloro-phenyl)-4-phenyl-piperidin-1-yl]-methanone The title compound, MS: m/e=512.2 ($M^+$), was prepared in accordance with the general method of example 1 from 3,5-bis(trifluoromethyl)benzoyl chloride and rac-cis-3-(4-chloro-phenyl)-4-phenyl-piperidine hydrochloride.

EXAMPLE 10

Rac-cis-(3,5-Bis-trifluoromethyl-phenyl)-{4-[3-(4-methyl-piperazin-1-yl)-phenyl]-3-phenyl-piperidin-1-yl}-methanone To a solution of rac-cis-(3,5-bis-trifluoromethyl-phenyl)-[4-(3-bromo-phenyl)-3-phenyl-piperidin-1-yl]-methanone (500 mg, 0.899 mmol) in 5 mL dry toluene was added 1-methyl-piperazine (0.123 mL, 1.08 mmol), sodium tert.-butoxide (125 mg, 1.26 mmol), bis(dibenzylidenacetone) palladium (2.1 mg, 0.002 mmol) and rac-2,2'-bis(diphenylphosphino)-1,1'-binaphthyl (4.3 mg, 0.007 mmol) and than refluxed overnight. The reaction mixture was diluted with 10 mL water and extracted three times with 20 mL ethyl acetate. Organic phases were pooled, dried with magnesium sulfate and evaporated. Flash chromatography on silica gel with hexane/ethyl acetate/triethyl amine 10:10:1 gave the desired product (196 mg, 38%), MS: m/e=576.1 ($M+H^+$).

EXAMPLE 11

Rac-cis-(3,5-Bis-trifluoromethyl-phenyl)-[4-(3-morpholin-4-yl-phenyl)-3-phenyl-piperidin-1-yl]-methanone The title compound, MS: m/e=563.3 ($M^+$), was prepared in accordance with the general method of example 10 from rac-cis-(3,5-bis-trifluoromethyl-phenyl)-[4-(3-bromo-phenyl)-3-phenyl-piperidin-1-yl]-methanone and morpholine.

EXAMPLE 12

Rac-cis-(3,5-Bis-trifluoromethyl-phenyl)-[3-phenyl-4-(3-phenylamino-phenyl)-piperidin-1-yl]-methanone The title compound, MS: m/e=569.2 (M$^+$), was prepared in accordance with the general method of example 10 from rac-cis-(3,5-bis-trifluoromethyl-phenyl)-[4-(3-bromo-phenyl)-3-phenyl-piperidin-1-yl]-methanone and aniline.

EXAMPLE 13

Rac-cis-(3,5-Bis-trifluoromethyl-phenyl)-[3-phenyl-4-(3-pyrrolidin-1-yl-phenyl)-piperidin-1-yl]-methanone The title compound, MS: m/e=547.2 (M$^+$), was prepared in accordance with the general method of example 10 from rac-cis-(3,5-bis-trifluoromethyl-phenyl)-[4-(3-bromo-phenyl)-3-phenyl-piperidin-1-yl]-methanone and pyrrolidine.

EXAMPLE 14

Rac-cis-(3,5-Bis-trifluoromethyl-phenyl)-{4-[3-(2-methoxy-ethylamino)-phenyl]-3-phenyl-piperidin-1-yl}-methanone The title compound, MS: m/e=551.1 (M$^+$), was prepared in accordance with the general method of example 10 from rac-cis-(3,5-bis-trifluoromethyl-phenyl)-[4-(3-bromo-phenyl)-3-phenyl-piperidin-1-yl]-methanone and 2-methoxy ethylamine.

EXAMPLE 15

Rac-cis-(3,5-Bis-trifluoromethyl-phenyl)-[4-(3-diethylamino-phenyl)-3-phenyl-piperidin-1-yl]-methanone The title compound, MS: m/e=549.2 (M$^+$), was prepared in accordance with the general method of example 10 from rac-cis-(3,5-bis-trifluoromethyl-phenyl)-[4-(3-bromo-phenyl)-3-phenyl-piperidin-1-yl]-methanone and diethylamine.

EXAMPLE 16

Rac-cis-(3,5-Bis-trifluoromethyl-phenyl)-{4-[3-(cyclopropylmethyl-amino)-phenyl]-3-phenyl-piperidin-1-yl}-methanone The title compound, MS: m/e=547.2 (M$^+$), was prepared in accordance with the general method of example 10 from rac-cis-(3,5-bis-trifluoromethyl-phenyl)-[4-(3-bromo-phenyl)-3-phenyl-piperidin-1-yl]-methanone and aminomethylcyclopropane.

EXAMPLE 17

Rac-cis-(3,5-Bis-trifluoromethyl-phenyl)-[4-(4-morpholin-4-yl-phenyl)-3-phenyl-piperidin-1-yl]-methanone The title compound, MS: m/e=563.3 (M$^+$), was prepared in accordance with the general method of example 10 from rac-cis-(3,5-bis-trifluoromethyl-phenyl)-[4-(4-chloro-phenyl)-3-phenyl-piperidin-1-yl]-methanone, morpholine and biphenyl-2-yl-dicyclohexyl-phosphane as ligand.

EXAMPLE 18

Rac-cis-(3,5-Bis-trifluoromethyl-phenyl)-{4-[4-(4-methyl-piperazin-1-yl)-phenyl]-3-phenyl-piperidin-1-yl}-methanone The title compound, MS: m/e=576.1 (M$^+$), was prepared in accordance with the general method of example 10 from rac-cis-(3,5-bis-trifluoromethyl-phenyl)-[4-(4-chloro-phenyl)-3-phenyl-piperidin-1-yl]-methanone, N-methyl-piperazine and biphenyl-2-yl-dicyclohexyl-phosphane as ligand.

EXAMPLE 19

Rac-cis-(3,5-Bis-trifluoromethyl-phenyl)-[3-phenyl-4-(4-pyrrolidin-1-yl-phenyl)-piperidin-1-yl]-methanone The title compound, MS: m/e=547.2 (M$^+$), was prepared in accordance with the general method of example 10 from rac-cis-(3,5-bis-trifluoromethyl-phenyl)-[4-(4-chloro-phenyl)-3-phenyl-piperidin-1-yl]-methanone, pyrrolidine and biphenyl-2-yl-dicyclohexyl-phosphane as ligand.

EXAMPLE 20

Rac-cis-(3,5-Bis-trifluoromethyl-phenyl)-{4-[4-(2-methoxy-ethylamino)-phenyl]-3-phenyl-piperidin-1-yl}-methanone The title compound, MS: m/e=551.1 (M$^+$), was prepared in accordance with the general method of example 10 from rac-cis-(3,5-bis-trifluoromethyl-phenyl)-[4-(4-chloro-phenyl)-3-phenyl-piperidin-1-yl]-methanone, 2-methoxy-ethylamine and biphenyl-2-yl-dicyclohexyl-phosphane as ligand.

EXAMPLE 21

Rac-cis-(3,5-Bis-trifluoromethyl-phenyl)-{3-[3-(3-methoxy-propylamino)-phenyl]-4-phenyl-piperidin-1-yl}-methanone The title compound, MS: m/e=565.4 (M$^+$), was prepared in accordance with the general method of example 10 from rac-cis-(3,5-bis-trifluoromethyl-phenyl)-[3-(3-chloro-phenyl)-4-phenyl-piperidin-1-yl]-methanone, 3-methoxy-propylamine and biphenyl-2-yl-dicyclohexyl-phosphane as ligand.

EXAMPLE 22

Rac-cis-(3,5-Bis-trifluoromethyl-phenyl)-[4-phenyl-3-(3-pyrrolidin-1-yl-phenyl)-piperidin-1-yl]-methanone The title compound, MS: m/e=547.4 (M$^+$), was prepared in accordance with the general method of example 10 from rac-cis-(3,5-bis-trifluoromethyl-phenyl)-[3-(3-chloro-phenyl)-4-phenyl-piperidin-1-yl]-methanone, pyrrolidine and biphenyl-2-yl-dicyclohexyl-phosphane as ligand.

EXAMPLE 23

Rac-cis-(3,5-Bis-trifluoromethyl-phenyl)-{4-[2-(2-methoxy-ethylamino)-phenyl]-3-phenyl-piperidin-1-yl}-methanone The title compound, MS: m/e=551.1 (M$^+$), was prepared in accordance with the general method of example 10 from rac-cis-(3,5-bis-trifluoromethyl-phenyl)-[4-(2-chloro-phenyl)-3-phenyl-piperidin-1-yl]-methanone, 2-methoxy-ethylamine and biphenyl-2-yl-dicyclohexyl-phosphane as ligand.

EXAMPLE 24

Rac-cis-(3,5-Bis-trifluoromethyl-phenyl)-{4-[2-(2-dimethylamino-ethylamino)-phenyl]-3-phenyl-piperidin-1-yl}-methanone The title compound, MS: m/e=564.3 (M$^+$), was prepared in accordance with the general method of example 10 from rac-cis-(3,5-bis-trifluoromethyl-phenyl)-[4-(2-chloro-phenyl)-3-phenyl-piperidin-1-yl]-methanone, N,N-dimethyl-ethylendiamine and biphenyl-2-yl-dicyclohexyl-phosphane as ligand.

EXAMPLE 25

Rac-cis-(3,5-Bis-trifluoromethyl-phenyl)-[3-(4-morpholin-4-yl-phenyl)-4-phenyl-piperidin-1-yl]-methanone The title compound, MS: m/e=563.3 (M$^+$), was prepared in accordance with the general method of example 10 from rac-cis-(3,5-bis-trifluoromethyl-phenyl)-[3-(4-chloro-phenyl)-4-phenyl-piperidin-1-yl]-methanone, morpholine and biphenyl-2-yl-dicyclohexyl-phosphane as ligand.

EXAMPLE 26

Rac-cis-(3,5-Bis-trifluoromethyl-phenyl)-(4-morpholin-4-yl-3-phenyl-piperidin-1-yl)-methanone To a mixture of 1-benzyl-3-phenyl-piperidin-4-one (2.07 g, 7.78 mmol) and morpholine (678 mg, 7.78 mmol) was added tetraisopropyl-orthotitanate (2.97 mL, 9.73 mmol) at room temperature. After stirring at room temperature overnight the reaction mixture was diluted with ethanol (8.0 mL) and sodium cyanoborohydride (369 mg, 5.37 mmol) was added. The reaction mixture was stirred at room temperature for 24 h and was diluted with water (2.0 mL). The inorganic precipitate was filtered off and washed with ethanol. The filtrate was evaporated and purified by flash chromatography on silica gel with toluene/ethyl acetate 6:1 to give rac-cis-4-(1-benzyl-3-phenyl-piperidin-4-yl)-morpholine (1.42 g, 54%) as a yellow solid, MS: m/e=337.3 (M+H$^+$).

Rac-cis-4-(1-benzyl-3-phenyl-piperidin-4-yl)-morpholine (1.3 g, 3.86 mmol) was dissolved in methanol (50 mL) and concentrated hydrochloric acid (0.2 mL) and palladium on charcoal (10%, 200 mg) were added. After stirring in a hydrogen atmosphere (1 bar) at room temperature overnight the mixture was filtered and the solvent was evaporated. The crude intermediate was dissolved in dichloromethane (20 mL) and triethylamine (2.69 mL, 19.3 mmol) and 3,5-bistrifluoromethyl-benzoyl chloride (0.91 mL, 5.02 mmol) were added. The reaction mixture was stirred at room temperature overnight and than diluted with 20 mL water. The organic phase was separated and the aqueous layer was extracted twice with 20 mL dichloromethane. Organic phases were pooled, dried with magnesium sulfate and evaporated. Flash chromatography on silica gel with hexane/ethyl acetate/triethyl amine 80:20:1 gave the desired product (1.57 g, 83%) as off-white crystals, MS: m/e=487.3 (M+H$^+$).

EXAMPLE 27

Rac-cis-(3,5-Bis-trifluoromethyl-phenyl)-[4-(4-methyl-piperazin-1-yl)-3-phenyl-piperidin-1-yl]-methanone The title compound, MS: m/e=500.2 (M+H$^+$), was prepared in accordance with the general method of example 26 from 1-benzyl-3-phenyl-piperidin-4-one, N-methyl-piperazine and 3,5-bistrifluoromethyl-benzoyl chloride.

EXAMPLE 28

Rac-cis-(3,5-Bis-trifluoromethyl-phenyl)-(4-morpholin-4-yl-3-o-tolyl-piperidin-1-yl)-methanone The title compound, MS: m/e=501.2 (M+H$^+$), was prepared in accordance with the general method of example 26 from 1-benzyl-3-o-tolyl-piperidin-4-one, morpholine and 3,5-bistrifluoromethyl-benzoyl chloride.

EXAMPLE 29

Rac-cis-(3,5-Bis-trifluoromethyl-phenyl)-[4-(4-methyl-piperazin-1-yl)-3-o-tolyl-piperidin-1-yl]-methanone The title compound, MS: m/e=514.3 (M+H$^+$), was prepared in accordance with the general method of example 26 from 1-benzyl-3-o-tolyl-piperidin-4-one, N-methyl-piperazine and 3,5-bistrifluoromethyl-benzoyl chloride.

EXAMPLE 30

Rac-cis-(3,5-Bis-trifluoromethyl-phenyl)-[3-(2-chloro-phenyl)-4-morpholin-4-yl-piperidin-1-yl]-methanone The title compound, MS: m/e=521.1 (M+H$^+$), was prepared in accordance with the general method of example 26 from 1-benzyl-3-(2-chloro-phenyl)-piperidin-4-one, morpholine and 3,5-bistrifluoromethyl-benzoyl chloride.

EXAMPLE 31

Rac-cis-(3,5-Bis-trifluoromethyl-phenyl)-[3-(2-chloro-phenyl)-4-(4-methyl-piperazin-1-yl)-piperidin-1-yl]-methanone The title compound, MS: m/e=534.2 (M+H$^+$), was prepared in accordance with the general method of example 26 from 1-benzyl-3-(2-chloro-phenyl)-piperidin-4-one, N-methyl-piperazine and 3,5-bistrifluoromethyl-benzoyl chloride.

EXAMPLE 32

Rac-cis-1-{4-[1-(3,5-Bis-trifluoromethyl-benzoyl)-3-phenyl-piperidin-4-yl]-piperazin-1-yl}-2,2,2-trifluoro-ethanone To a mixture of 1-benzyl-3-phenyl-piperidin-4-one (10.0 g, 37.7 mmol) and piperazine (13.0 g, 151 mmol) was added tetraisopropyl-orthotitanate (42.8 mL, 151 mmol) at room temperature. After stirring at room temperature overnight the reaction mixture was diluted with ethanol (300 mL) and sodium cyanoborohydride (10.5 g, 151 mmol) was added. The reaction mixture was stirred at room temperature for 24 h and was diluted with water (10 mL). The inorganic precipitate was filtered off and washed with ethanol. The solvent was evaporated and the residue was taken up in ethylenglycol (130 mL) and sodium hydroxide (13.6 g, 37.7 mmol) was added. The reaction mixture was stirred at 130° C. for 15 min. After cooling water (200 mL) was added and the mixture was extracted twice with 200 mL diethylether. Organic phases were pooled, dried with magnesium sulfate and evaporated. Flash chromatography on silica gel with methylene chloride/triethyl amine 99:1 gave rac-cis-1-(1- benzyl-3-phenyl-piperidin-4-yl)-piperazine (4.63 g, 36%), as a yellow oil, MS: m/e=336.3 (M+H$^+$).

Rac-cis-1-(1-benzyl-3-phenyl-piperidin-4-yl)-piperazine (4.62 g, 13.8 mmol) was dissolved in methylene chloride (100 mL) and 4-dimethylaminopyridine (29 mg, 0.14 mmol) was added. The reaction mixture was cooled with an ice bath and pyridine (2.78 mL, 34.4 mmol) and trifluoroacetic acid anhydride (2.68 mL, 19.3 mmol) were added sequentially. The mixture was stirred at room temperature overnight and water (100 mL) was added. The organic phase was separated and the aqueous layer was extracted twice with 100 mL methylene chloride. Organic phases were pooled, dried with magnesium sulfate and evaporated. Flash chromatography on silica gel with hexane/ethyl acetate/triethyl amine 90:10:1 gave rac-cis-1-[4-(1-benzyl-3-phenyl-piperidin-4-yl)-piperazin-1-yl]-2,2,2-trifluoro-ethanone (4.64 g, 78%) as a light yellow oil, MS: m/e=432.5 (M+H$^+$).

Rac-cis-1-[4-(1-benzyl-3-phenyl-piperidin-4-yl)-piperazin-1-yl]-2,2,2-trifluoro-ethanone (4.60 g, 10.7 mmol) was dissolved in methanol (200 mL) and concentrated hydrochloric acid (1.0 mL) and palladium on charcoal (10%, 700 mg) were added. After stirring in a hydrogen atmosphere (1 bar) at room temperature overnight the mixture was filtered and the solvent was evaporated. The crude intermediate was dissolved in dichloromethane (100 mL) and triethylamine (7.25 mL, 51.7 mmol) and 3,5-bistrifluoromethyl-benzoyl chloride (2.06 mL, 11.4 mmol) were added. The reaction mixture was stirred at room temperature overnight and than diluted with 100 mL water. The organic phase was separated and the aqueous layer was extracted twice with 100 mL dichloromethane. Organic phases were pooled, dried with magnesium sulfate and evaporated. Flash chromatography on silica gel with hexane/ethyl acetate/triethyl amine 90:10:1 gave the desired product (5.26 g, 87%) as a white foam, MS: m/e=582.0 (M+H$^+$).

EXAMPLE 33

Rac-cis-{4-[4-(3,5-Bis-trifluoromethyl-benzoyl)-piperazin-1-yl]-3-phenyl-piperidin-1-yl}-(3,5-bis-trifluoromethyl-phenyl)-methanone The title compound, MS: m/e=726.1 (M+H$^+$), was obtained as a by-product of rac-cis-1-{4-[1-(3,5-bis-trifluoromethyl-benzoyl)-3-phenyl-piperidin-4-yl]-piperazin-1-yl}-2,2,2-trifluoro-ethanone (example 32).

EXAMPLE 34

Rac-cis-(3,5-Bis-trifluoromethyl-phenyl)-(3-phenyl-4-piperazin-1-yl-piperidin-1-yl)-methanone Rac-cis-1-{4-[1-(3,5-Bis-trifluoromethyl-benzoyl)-3-phenyl-piperidin-4-yl]-piperazin-1-yl}-2,2,2-trifluoro-ethanone (4.15 g, 7.14 mmol) was dissolved in methanol (25 mL). Water (1 mL) and potassium carbonate (2.96 g, 21.4 mmol) were added and the reaction mixture was stirred at room temperature for 4 h. Water (100 mL) was added and the mixture was extracted twice with 200 mL methylene chloride. Organic phases were pooled and dried with magnesium sulfate. Evaporation of the solvent gave the title compound (3.4 g, 98%) as a white foam which was used without any further purification, MS: m/e=486.3 (M+H$^+$).

EXAMPLE 35

Rac-cis-2{4-[1-(3,5-Bis-trifluoromethyl-benzoyl)-3-phenyl-piperidin-4-yl]-piperazin-1-yl}-N,N-dimethyl-acetamide Rac-cis-(3,5-Bis-trifluoromethyl-phenyl)-(3-phenyl-4-piperazin-1-yl-piperidin-1-yl)-methanone (200 mg, 0.41 mmol) was dissolved in N,N-dimethylformamide (5 mL). Potassium carbonate (171 mg, 1.24 mmol) and 2-chloro-N,N-dimethylacetamide (0.042 mL, 0.41 mmol) were added and the reaction mixture was stirred at room temperature overnight. Water (50 mL) was added and the mixture was extracted twice with 100 mL ethyl acetate. Organic phases were pooled, dried with magnesium sulfate and evaporated. Chromatography on silica gel with methylen chloride/methanol/triethyl amine 90:10:1 gave the desired product (200 mg, 85%) as an off-white solid, MS: m/e=571.1 (M+H$^+$).

EXAMPLE 36

Rac-cis-(3,5-Bis-trifluoromethyl-phenyl)-[4-(4-cyclopropylmethyl-piperazin-1-yl)-3-phenyl-piperidin-1-yl]-methanone The title compound, MS: m/e=540.3 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and bromomethyl cyclopropane.

EXAMPLE 37

Rac-cis-[4-(4-Benzyl-piperazin-1-yl)-3-phenyl-piperidin-1-yl]-(3,5-bis-trifluoromethyl-phenyl)-methanone The title compound, MS: m/e=576.1 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and benzyl bromide.

EXAMPLE 38

Rac-cis-1-{4-[1-(3,5-Bis-trifluoromethyl-benzoyl)-3-phenyl-piperidin-4-yl]-piperazin-1-yl}-ethanone Rac-cis-(3,5-Bis-trifluoromethyl-phenyl)-(3-phenyl-4-piperazin-1-yl-piperidin-1-yl)-methanone (200 mg, 0.41 mmol) was dissolved in methylene chloride (5 mL). Triethyl amine (0.173 mL, 1.24 mmol) and acetyl chloride (0.035 mL, 0.49 mmol) were added and the reaction mixture was stirred at room temperature overnight. The solvent was evaporated and chromatography on silica gel with methylen chloride/triethyl amine 99:1 gave the desired product (122 mg, 56%) as a light yellow foam, MS: m/e=528.2 (M+H$^+$).

EXAMPLE 39

Rac-cis-(3,5-Bis-trifluoromethyl-phenyl)-[4-(4-cyclopropanecarbonyl-piperazin-1-yl)-3-phenyl-piperidin-1-yl]-methanone The title compound, MS: m/e=554.2 (M+H$^+$), was prepared in accordance with the general method of example 38 from rac-cis-(3,5-bis-trifluoromethyl-phenyl)-(3-phenyl-4-piperazin-1-yl-piperidin-1-yl)-methanone and cyclopropane carboxylic acid chloride.

EXAMPLE 40

Rac-cis-[4-(4-Benzoyl-piperazin-1-yl)-3-phenyl-piperidin-1-yl]-(3,5-bis-trifluoromethyl-phenyl)-methanone The title compound, MS: m/e=590.2 (M+H$^+$), was prepared in accordance with the general method of example 38 from rac-cis-(3,5-bis-trifluoromethyl-phenyl)-(3-phenyl-4-piperazin-1-yl-piperidin-1-yl)-methanone and benzoyl chloride.

EXAMPLE 41

Rac-cis-{4-[1-(3,5-Bis-trifluoromethyl-benzoyl)-3-phenyl-piperidin-4-yl]-piperazin-1-yl}-morpholin-4-yl-methanone The title compound, MS: m/e=599.1 (M+H$^+$), was prepared in accordance with the general method of example 38 from rac-cis-(3,5-bis-trifluoromethyl-phenyl)-(3-phenyl-4-piperazin-1-yl-piperidin-1-yl)-methanone and 4-morpholine carbonyl chloride.

EXAMPLE 42

Rac-cis-4-[1-(3,5-Bis-trifluoromethyl-benzoyl)-3-phenyl-piperidin-4-yl]-piperazine-1-carboxylic acid 2-dimethylamino-ethyl ester The title compound, MS: m/e=601.1 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and N-(2-chloroethyl)-N,N-dimethylamine.

EXAMPLE 43

Rac-cis-(3,5-Bis-trifluoromethyl-phenyl)-[4-(4-cyclopropyl-piperazin-1-yl)-3-phenyl-piperidin-1-yl]-methanone The title compound, MS: m/e=526.1 (M+H$^+$), was prepared in accordance with the general method of example 26 from 1-benzyl-3-phenyl-piperidin-4-one, N-cyclopropyl-piperazine and 3,5-bistrifluoromethyl-benzoyl chloride.

EXAMPLE 44

Rac-cis-(3,5-Bis-trifluoromethyl-phenyl)-(4-hydroxy-3'-phenyl-[1,4']bipiperidinyl-1'-yl)-methanone The title compound, MS: m/e=501.2 (M+H$^+$), was prepared in accordance with the general method of example 26 from 1-benzyl-3-phenyl-piperidin-4-one, 4-hydroxy-piperidine and 3,5-bistrifluoromethyl-benzoyl chloride.

EXAMPLE 45

Rac-cis-(3,5-Bis-trifluoromethyl-phenyl)-[3-(4-fluoro-phenyl)-4-(4-methyl-piperazin-1-yl)-piperidin-1-yl]-methanone The title compound, MS: m/e=518.2 (M+H$^+$), was prepared in accordance with the general method of example 26 from 1-benzyl-3-(4-fluoro-phenyl)-piperidin-4-one, N-methyl-piperazine and 3,5-bistrifluoromethyl-benzoyl chloride.

EXAMPLE 46

Rac-cis-(3,5-Bis-trifluoromethyl-phenyl)-[3-(4-fluoro-phenyl)-4-morpholin-4-yl-piperidin-1-yl]-methanone The title compound, MS: m/e=505.3 (M+H$^+$), was prepared in accordance with the general method of example 26 from 1-benzyl-3-(4-fluoro-phenyl)-piperidin-4-one, morpholine and 3,5-bistrifluoromethyl-benzoyl chloride.

EXAMPLE 47

Rac-cis-2-{4-[1-(3,5-Bis-trifluoromethyl-benzoyl)-3-phenyl-piperidin-4-yl]-piperazin-1-yl}-N-(2,6-dimethyl-phenyl)-acetamide The title compound, MS: m/e=647.2 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and N-chloroacetyl-2,6-dimethylaniline.

EXAMPLE 48

(3R,3'R,4S)- and (3S,3'R,4R)-(3,5-Bis-trifluoromethyl-phenyl)-[4-(3'-hydroxy-pyrrolidin-1'-yl)-3-phenyl-piperidin-1-yl]-methanone A mixture of the title compounds, MS: m/e=487.3 (M+H$^+$), was prepared in accordance with the general method of example 26 from 1-benzyl-3-phenyl-piperidin-4-one, (R)-3-hydroxypyrrolidine and 3,5-bistrifluoromethyl-benzoyl chloride.

EXAMPLE 49

Rac-cis-(3,5-Bis-trifluoromethyl-phenyl)-(3-phenyl-4-thiomorpholin-4-yl-piperidin-1-yl)-methanone The title compound, MS: m/e=503.2 (M+H$^+$), was prepared in accordance with the general method of example 26 from 1-benzyl-3-phenyl-piperidin-4-one, thiomorpholine and 3,5-bistrifluoromethyl-benzoyl chloride.

EXAMPLE 50

Rac-cis-(3,5-Bis-trifluoromethyl-phenyl)-[4-(1-oxo-1λ4-thiomorpholin-4-yl)-3-phenyl-piperidin-1-yl]-methanone Rac-cis-(3,5-Bis-trifluoromethyl-phenyl)-(3-phenyl-4-thiomorpholin-4-yl-piperidin-1-yl)-methanone (190 mg, 0.38 mmol) was dissolved in methanol (5 mL). Potassium peroxymonosulfat (Oxone®) (140 mg, 0.23 mmol) was added and the reaction mixture was stirred at room temperature for 3 days. The salts were filtered off and the filtrate was evaporated. Chromatography on silica gel with methylen chloride/methanol/triethyl amine 98:1:1 gave the desired product (163 mg, 83%) as an off-white solid, MS: m/e=519.2 (M+H$^+$).

EXAMPLE 51

Rac-cis-(3,5-Bis-trifluoromethyl-phenyl)-[4-(1,1-dioxo-1λ6-thiomorpholin-4-yl)-3-phenyl-piperidin-1-yl]-methanone Rac-cis-(3,5-Bis-trifluoromethyl-phenyl)-(3-phenyl-4-thiomorpholin-4-yl-piperidin-1-yl)-methanone (200 mg, 0.40 mmol) was dissolved in methanol (5 mL). Potassium peroxymonosulfate (Oxone®) (540 mg, 0.88 mmol) was added and the reaction mixture was stirred at room temperature for 3 days. Sodium hydrogen sulfite solution (40%, 5 mL) was added and the mixture was stirred at room temperature for 30 min. Sodium bicarbonate solution (2N, 20 mL) was added and the mixture was extracted three times with methylen chloride (30 mL). Organic phases were pooled, dried with magnesium sulfate and evaporated. Flash chromatography on silica gel with hexane/ethyl acetate/triethyl amine 10:90:1 gave the desired product (204 mg, 96%) as a white foam, MS: m/e=535.2 (M+H$^+$).

EXAMPLE 52

Rac-cis-(3,5-Bis-trifluoromethyl-phenyl)-[3-(4-chloro-phenyl)-4-morpholin-4-yl-piperidin-1-yl]-methanone To a mixture of 1-benzyl-3-(4-chloro-phenyl)-piperidin-4-one (1.0 g, 3.34 mmol) and morpholine (1.16 mL, 13.3 mmol) was added tetraisopropyl-orthotitanate (3.95 mL, 13.3 mmol) at room temperature. After stirring at room temperature overnight the reaction mixture was diluted with ethanol (30.0 mL) and sodium cyanoborohydride (930 mg, 13.3 mmol) was added. The reaction mixture was stirred at room temperature for 24 h and was diluted with water (2.0 mL). The inorganic precipitate was filtered off and washed with ethanol. The filtrate was evaporated and purified by flash chromatography on silica gel with hexane/ethyl acetate/triethylamine 40:10:1 to give rac-cis-4-[1-benzyl-3-(4-chloro-phenyl)-piperidin-4-yl]-morpholine (650 mg, 52%) as a yellow solid, MS: m/e=371.3 (M+H$^+$).

Rac-cis-4-[1-benzyl-3-(4-chloro-phenyl)-piperidin-4-yl]-morpholine (650 mg, 1.75 mmol) was dissolved in dichloromethane (15 mL) and 1-chloroethyl-chloroformate (0.575 mL, 5.27 mmol) were added at 0° C. The reaction mixture was refluxed overnight. Methanol (15 mL) was added and reflux was continued for 3 h. The solvents were evaporated. The crude intermediate was dissolved in dichloromethane (30 mL) and triethylamine (1.22 mL, 8.75 mmol) and 3,5-bistrifluoromethyl-benzoyl chloride (0.35 mL, 1.93 mmol) were added. The reaction mixture was stirred at room temperature overnight and than diluted with 50 mL water. The organic phase was separated and the aqueous layer was extracted twice with 50 mL dichloromethane. Organic phases were pooled, dried with magnesium sulfate and evaporated. Flash chromatography on silica gel with hexane/ethyl acetate/triethylamine 20:10.1 gave the desired product (820 mg, 90%) as a yellow solid, MS: m/e=521.1 (M+H$^+$).

EXAMPLE 53

Rac-cis-(3,5-Bis-trifluoromethyl-phenyl)-(4-cyclopropylmethoxy-3'-phenyl-[1,4']bipiperidinyl-1'-yl)-methanone Rac-cis-(3,5-Bis-trifluoromethyl-phenyl)-(4-hydroxy-3'-phenyl-[1,4']bipiperidinyl-1'-yl)-methanone (100 mg, 0.20 mmol) was dissolved in dimethylformamide (2 mL). Sodium hydride (17 mg, 55%, 0.40 mmol) and bromomethyl cyclopropane (0.038 mL, 0.40 mmol) were added and the reaction mixture was stirred at room temperature overnight. Water (5 mL) was added and the mixture was extracted three times with ethyl acetate (20 mL). Organic phases were pooled, dried with magnesium sulfate and evaporated. Chromatography on silica gel with methylene chloride/methanol/triethyl amine 98:1:1 gave the desired product (95 mg, 85%) as an off-white solid, MS: m/e=555.1 (M+H$^+$).

EXAMPLE 54

(3R,3'R,4S)- and (3S,3'R,4R)-(3,5-Bis-trifluoromethyl-phenyl)-[4-(3-cyclopropylmethoxy-pyrrolidin-1-yl)-3-phenyl-piperidin-1-yl]-methanone A mixture of the title compounds, MS: m/e=541.2 (M+H$^+$), was prepared in accordance with the general method of example 53 from (3R,3'R,4R)- and (3S,3'R,4S)-(3,5-bis-trifluoromethyl-phenyl)-[4-(3'-hydroxy-pyrrolidin-1'-yl)-3-phenyl-piperidin-1-yl]-methanone and bromomethyl cyclopropane.

EXAMPLE 55

Rac-cis-1'-(3,5-Bis-trifluoromethyl-benzoyl)-3'-phenyl-[1,4']bipiperidinyl-4-one Rac-cis-(3,5-Bis-trifluoromethyl-phenyl)-(4-hydroxy-3'-phenyl-[1,4']bipiperidinyl-1'-yl)-methanone (1.02 g, 2.04 mmol) was dissolved in methylene chloride (10 mL). Oxalyl chloride (0.21 mL, 2.45 mmol) and dimethylsulfoxide (0.29 mL, 4.07 mmol) were added at −78° C. and the reaction mixture was stirred at −78° C. for 3 h. Triethyl amine (1.14 mL, 8.15 mmol) was added and the reaction mixture was slowly warmed to room temperature. Stirring was continued at room temperature overnight. Water (10 mL) was added and the mixture was extracted three times with methylene chloride (20 mL). Organic phases were pooled, dried with magnesium sulfate and evaporated. Flash chromatography on silica gel with hexane/ethyl acetate/triethyl amine 70:30:1 gave the desired product (584 mg, 57%) as a white foam, MS: m/e=499.2 (M+H$^+$).

EXAMPLE 56

Rac-cis-1-[1-(3,5-Bis-trifluoromethyl-benzoyl)-3-phenyl-piperidin-4-yl]-pyrrolidin-3-one The title compound, MS: m/e=485.3 (M+H$^+$), was prepared in accordance with the general method of example 55 from (3R,3'R,4R)- and (3S,3'R,4S)-(3,5-bis-trifluoromethyl-phenyl)-[4-(3'-hydroxy-pyrrolidin-1'-yl)-3-phenyl-piperidin-1-yl]-methanone.

EXAMPLE 57

Rac-cis-(3,5-Bis-trifluoromethyl-phenyl)-(4,4-difluoro-3'-phenyl-[1,4']bipiperidinyl-1'-yl)-methanone Rac-cis-1'-(3,5-Bis-trifluoromethyl-benzoyl)-3'-phenyl-[1,4']bipiperidinyl-4-one (183 mg, 0.367 mmol) was dissolved in methylene chloride (5 mL). Diethylamino sulfurtrifluoride (0.062 mL, 0.50 mmol) was added at −78°. The reaction mixture was stirred at −78° C. for 3 h then slowly warmed to room temperature and stirring was continued at room temperature overnight. The solvent was evaporated and chromatography on silica gel with hexane/ethyl acetate/triethyl amine 10:10:1 gave the desired product (83 mg, 43%) as an off-white solid, MS: m/e=521.2 (M+H$^+$).

EXAMPLE 58

(3RS,3'RS,4SR)- and (3RS,3'SR,4SR)-(3,5-Bis-trifluoromethyl-phenyl)-[3'-(4-fluoro-phenyl)-3-hydroxy-[1,4']bipiperidinyl-1'-yl]-methanone The title compound, MS: m/e=519.2 (M+H$^+$), was prepared in accordance with the general method of example 26 from 1-benzyl-3-(4-fluoro-phenyl)-piperidin-4-one, (rac)-3-hydroxy-piperidine and 3,5-bistrifluoromethyl-benzoyl chloride.

EXAMPLE 59

Rac-cis-(3,5-Bis-trifluoromethyl-phenyl)-[3-phenyl-4-(4-pyrimidin-2-yl-piperazin-1-yl)-piperidin-1-yl]-methanone Rac-cis-(3,5-Bis-trifluoromethyl-phenyl)-(3-phenyl-4-piperazin-1-yl-piperidin-1-yl)-methanone (300 mg, 0.62 mmol) and 2-chloropyrimidine (71 mg, 0.68) were stirred at 100° C. overnight. The reaction mixture was taken up in 1 mL methylene chloride and chromatographed on silica gel with methylen chloride/methanol/triethyl amine 90:10:1. The desired product (181 mg, 47%) was a light yellow solid, MS: m/e=564.3 (M+H$^+$).

EXAMPLE 60

Rac-cis-(3,5-Bis-trifluoromethyl-phenyl)-[3-phenyl-4-(2,3,5,6-tetrahydro-[1,2']bipyrazinyl-4-yl)-piperidin-1-yl]-methanone The title compound, MS: m/e=564.3 (M+H$^+$), was prepared in accordance with the general method of example 59 from rac-cis-(3,5-bis-trifluoromethyl-phenyl)-(3-phenyl-4-piperazin-1-yl-piperidin-1-yl)-methanone and 2-chloropyrazine.

EXAMPLE 61

Rac-cis-(3,5-Bis-trifluoromethyl-phenyl)-[4-(3,3-difluoro-pyrrolidin-1-yl)-3-phenyl-piperidin-1-yl]-methanone The title compound, MS: m/e=507.5 (M+H$^+$), was prepared in accordance with the general method of example 57 from rac-cis-1-[1-(3,5-Bis-trifluoromethyl-benzoyl)-3-phenyl-piperidin-4-yl]-pyrrolidin-3-one.

EXAMPLE 62

Rac-cis-(3,5-Bis-trifluoromethyl-phenyl)-[3-(4-fluoro-phenyl)-4-pyrrolidin-1-yl-piperidin-1-yl]-methanone The title compound, MS: m/e=489.3 (M+H$^+$), was prepared in accordance with the general method of example 26 from 1-benzyl-3-(4-fluoro-phenyl)-piperidin-4-one, pyrrolidine and 3,5-bistrifluoromethyl-benzoyl chloride.

EXAMPLE 63

Rac-cis-(3,5-Bis-trifluoromethyl-phenyl)-[3'-(4-chloro-phenyl)-4-hydroxy-[1,4']bipiperidinyl-1'-yl]-methanone To a mixture of 1-benzyl-3-(4-chloro-phenyl)-piperidin-4-one (3.32 g, 11.1 mmol) and 4-hydroxy-piperidine (1.23 g, 12.2 mmol) was added tetraisopropyl-orthotitanate (3.94 g, 13.8 mmol) at room temperature. After stirring at room temperature overnight the reaction mixture was diluted with ethanol (30.0 mL) and sodium cyanoborohydride (905 mg, 14.4 mmol) was added. The reaction mixture was stirred at room temperature for 24 h and was diluted with water (2.0 mL). The inorganic precipitate was filtered off and washed with ethanol. The filtrate was evaporated and purified by flash chromatography on silica gel with dichloromethane/methanol/ammonia 100:4:0.4 to give rac-cis-1'-benzyl-3'-(4-chloro-phenyl)-[1,4']bipiperidinyl-4-ol (2.25 g, 53%) as a white foam, MS: m/e=385.3 (M+H$^+$).

Rac-cis-1'-benzyl-3'-(4-chloro-phenyl)-[1,4'] bipiperidinyl-4-ol (2.17 g, 5.64 mmol) was dissolved in dimethylformamide (8 mL) and imidazole (1.15 g, 16.9 mmol) and tert.butyl-dimethyl-silylchloride (1.70 g, 11.3 mmol) were added. The reaction mixture was stirred at 40° C. overnight and than diluted with 50 mL water. The mixture was extracted three times with 50 mL ethyl acetate. Organic phases were pooled, dried with magnesium sulfate and evaporated. Flash chromatography on silica gel with hexane/ethyl acetate/triethyl amine 80:10:1 gave rac-cis-1'-benzyl-4-(tert-butyl-dimethyl-silanyloxy)-3'-(4-chloro-phenyl)-[1,4']bipiperidinyl (2.80 g, 99%) as a colorless oil, MS: m/e=499.3 (M$^+$).

Rac-cis-1'-benzyl-4-(tert-butyl-dimethyl-silanyloxy)-3'-(4-chloro-phenyl)-[1,4']bipiperidinyl (2.80 g, 5.60 mmol) were dissolved in dichloromethane (45 mL) and 1-chloroethyl-chloroformate (1.83 mL, 16.8 mmol) were added at 0° C. The reaction mixture was refluxed overnight. Methanol (40 mL) was added and reflux was continued for 3 h. The solvents were evaporated. The crude intermediate was dissolved in dichloromethane (100 mL) and triethylamine (3.9 mL, 28 mmol) and 3,5-bistrifluoromethyl-benzoyl chloride (1.11 mL, 6.16 mmol) were added. The reaction mixture was stirred at room temperature overnight and than diluted with 50 mL water. The organic phase was separated and the aqueous layer was extracted twice with 50 mL dichloromethane. Organic phases were pooled, dried with magnesium sulfate and evaporated. Flash chromatography on silica gel with dichloromethane/methanol/ammonia 140:10:1 gave the desired product (1.57 g, 83%) as a white foam, MS: m/e=535.2 (M+H$^+$).

EXAMPLE 64

Rac-cis-4-[1-(3,5-Bis-trifluoromethyl-benzoyl)-3-phenyl-piperidin-4-yl]-piperazine-1-carboxylic Acid Diethylamide The title compound, MS: m/e=584.2 (M+H$^+$), was prepared in accordance with the general method of example 38 from rac-cis-(3,5-bis-trifluoromethyl-phenyl)-(3-phenyl-4-piperazin-1-yl-piperidin-1-yl)-methanone and diethyl carbonyl chloride.

EXAMPLE 65

(+)-(3,5-Bis-trifluoromethyl-phenyl)-[4-(4-cyclopropanecarbonyl-piperazin-1-yl)-3-phenyl-piperidin-1-yl]-methanone Rac-cis-(3,5-Bis-trifluoromethyl-phenyl)-[4-(4-cyclopropanecarbonyl-piperazin-1-yl)-3-phenyl-piperidin-1-yl]-methanone was separated on Chiralpak AD® available from Merck Eurolab with 10% ethanol in heptane. The second fraction contained the more active enantiomer, $[\alpha]_{589}^{20}$=+18.18 (c=0.9679, methanol).

EXAMPLE 66

Rac-cis-(3,5-Bis-trifluoromethyl-phenyl)-[3'-(4-chloro-phenyl)-4-cyclopropylmethoxy-[1,4'] bipiperidinyl-1'-yl]-methanone The title compound, MS: m/e=589.2 (M+H$^+$), was prepared in accordance with the general method of example 53 from rac-cis-(3,5-bis-trifluoromethyl-phenyl)-[3'-(4-chloro-phenyl)-4-hydroxy-[1,4']bipiperidinyl-1'-yl]-methanone and bromomethyl cyclopropane.

EXAMPLE 67

Rac-cis-1'-(3,5-Bis-trifluoromethyl-benzoyl)-3'-(4-chloro-phenyl)-[1,4']bipiperidinyl-4-one The title compound, MS. m/e=533.2 (M+H$^+$), was prepared in accordance with the general method of example 55 from rac-cis-(3,5-bis-trifluoromethyl-phenyl)-[3'-(4-chloro-phenyl)-4-hydroxy-[1,4']bipiperidinyl-1'-yl]-methanone.

EXAMPLE 68

Rac-cis-2-{4-[1-(3,5-Bis-trifluoromethyl-benzoyl)-3-phenyl-piperidin-4-yl]-piperazin-1-yl}-N-(4-fluoro-phenyl)-acetamide The title compound, MS: m/e=637.1 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and α-chloro-4-fluoroacetamide.

EXAMPLE 69

Rac-cis-2-{4-[1-(3,5-Bis-trifluoromethyl-benzoyl)-3-phenyl-piperidin-4-yl]-piperazin-1-yl}-1-morpholin-4-yl-ethanone The title compound, MS: m/e=613.1 (M+H$^+$), was prepared in accordance with the general method of example 35 from rac-cis-(3,5-bis-trifluoromethyl-phenyl)-(3-phenyl-4-piperazin-1-yl-piperidin-1-yl)-methanone and 4-(2-chloroacetyl)morpholine.

EXAMPLE 70

(−)-(3,5-Bis-trifluoromethyl-phenyl)-[3-(4-chloro-phenyl)-4-morpholin-4-yl-piperidin-1-yl]-methanone Rac-cis)-(3,5-Bis-trifluoromethyl-phenyl)-[3-(4-chloro-phenyl)-4-morpholin-4-yl-piperidin-1-yl]-methanone was separated on Chiralpak AD® available from Merck EurolabChiralpak with 15% ethanol in heptane. The second fraction contained the more active enantiomer, $[\alpha]_{589}^{20}$=−48.61 (c=0.5678, methanol).

EXAMPLE 71

Rac-cis-1-{4-[1-(3,5-Bis-trifluoromethyl-benzoyl)-3-phenyl-piperidin-4-yl]-piperazin-1-yl}-2-phenyl-ethanone The title compound, MS: m/e=604.1 (M+H$^+$), was prepared in accordance with the general method of example 38 from rac-cis-(3,5-bis-trifluoromethyl-phenyl)-(3-phenyl-4-piperazin-1-yl-piperidin-1-yl)-methanone and phenylacetyl-chloride.

EXAMPLE 72

Rac-cis-(3,5-Bis-trifluoromethyl-phenyl)-[3-(4-chloro-phenyl)-4-pyrrolidin-1-yl-piperidin-1-yl]-methanone The title compound, MS: m/e=505.2 (M+H$^+$), was prepared in accordance with the general method of example 52 from 1-benzyl-3-(4-chloro-phenyl)-piperidin-4-one, pyrrolidine and 3,5-bistrifluoromethyl-benzoyl chloride.

EXAMPLE 73

(3R,3'R,4S)- and (3S,3'R,4R)-(3,5-Bis-trifluoromethyl-phenyl)-[3-(4-fluoro-phenyl)-4-(3-hydroxy-pyrrolidin-1-yl)-piperidin-1-yl]-methanone A mixture of the title compounds, MS: m/e=505.2 (M+H$^+$), was prepared in accordance with the general method of example 26 from 1-benzyl-3-(4-fluoro-phenyl)-piperidin-4-one, (R)-3-hydroxypyrrolidine and 3,5-bistrifluoromethyl-benzoyl chloride.

EXAMPLE 74

Rac-cis-[4-(4-Benzooxazol-2-yl-piperazin-1-yl)-3-phenyl-piperidin-1-yl]-(3,5-bis-trifluoromethyl-phenyl)-methanone The title compound, MS: m/e=603.0 (M+H$^+$), was prepared in accordance with the general method of example 59 from rac-cis-(3,5-bis-trifluoromethyl-phenyl)-(3-phenyl-4-piperazin-1-yl-piperidin-1-yl)-methanone and 2-chlorobenzoxazole.

EXAMPLE 75

(1'R,3R,4R)- and (1'R,3S,4S)4-[1-(3,5-Bis-trifluoromethyl-benzoyl)-3-phenyl-piperidin-4-yl]-piperazine-1-carboxylic acid (1-phenyl-ethyl)-amide Rac-cis-(3,5-Bis-trifluoromethyl-phenyl)-(3-phenyl-4-piperazin-1-yl-piperidin-1-yl)-methanone (204 mg, 0.42 mmol) was dissolved in methylene chloride (5 mL). (R)-alpha-Methylbenzyl-isocyanate (0.066 mL, 0.46 mmol) was added and the reaction mixture was stirred at room temperature overnight. The solvent was evaporated and the product (256 mg, 96%) was obtained as an off-white foam, MS: m/e=633.1 (M+H$^+$).

EXAMPLE 76

(3RS,3'αRS,4SR)- and (3RS,3'SR,4SR)-Cyclopropanecarboxylic acid{1-[1-(3,5-bis-trifluoromethyl-benzoyl)-3-phenyl-piperidin-4-yl]-pyrrolidin-3-yl}-methyl-amide Rac-cis-1-[1-(3,5-Bis-trifluoromethyl-benzoyl)-3-phenyl-piperidin-4-yl]-pyrrolidin-3-one (767 mg, 1.58 mmol) was dissolved in ethanol (15 mL). Methylamine hydrochloride (139 mg, 2.06 mmol), triethylamine (417 mg, 4.12 mmol) and tetraisopropyl-orthotitanate (675 mg, 2.38 mmol) were added. After stirring at room temperature sodium borohydride (102 mg, 2.69 mmol) was added. The reaction mixture was stirred at room temperature for 24 h and was diluted with water (2.0 mL). The inorganic precipitate was filtered off and washed with ethanol. The filtrate was evaporated and purified by flash chromatography on silica gel with methylene chloride/methanol/triethylamine 98:1:1 to give (3RS,3'RS,4SR)- and (3RS,3'SR,4SR)-[4-(3-methyl-amino-pyrrolidin-1-yl)-3-(4-fluoro-phenyl)-piperidin-1-yl]-(3,5-bis-trifluoromethyl-phenyl)-methanone (174 mg, 22%) as a brown foam which was not further characterized.

(3RS,3'RS,4SR)- and (3RS,3'SR,4SR)-[4-(3-methyl-amino-pyrrolidin-1-yl)-3-(4-fluoro-phenyl)-piperidin-1-yl]-(3,5-bis-trifluoromethyl-phenyl)-methanone was reacted with cyclopropane carboxylic acid chloride as describe in example 38 to obtain the title compound, MS: m/e=568.2 (M+H$^+$).

EXAMPLE 77

(3RS,3'RS,4SR)- and (3RS,3'SR,4SR)-Cyclopropanecarboxylic acid [1'-(3,5-bis-trifluoromethyl-benzoyl)-3'-(4-fluoro-phenyl)-[1,4']bipiperidinyl-3-yl]-amide (3RS,3'RS,4SR)- and (3RS,3'SR,4SR)-(3,5-Bis-trifluoromethyl-phenyl)-[3'-(4-fluoro-phenyl)-3-hydroxy-[1,4']bipiperidinyl-1'-yl]-methanone (1.39 g, 2.68 mmol) was dissolved in dichloromethane (15 mL) and triethylamine (0.934 mL, 6.70 mmol) and methanesulfonyl chloride (0.292 mL, 3.75 mmol) were added at room temperature. The reaction mixture was stirred at room temperature for 30 min and than diluted with 20 mL water. The organic phase was separated and the aqueous layer was extracted twice with 30 mL dichloromethane. Organic phases were pooled, dried with magnesium sulfate and evaporated. Flash chromatography on silica gel with cyclohexane/ethyl acetate/triethylamine 90:10:1 gave (3RS,3'RS,4SR)- and (3RS,3'SR,4SR)-(3,5-bis-trifluoromethyl-phenyl)-[3-chloro-3'-(4-fluoro-phenyl)-[1,4']bipiperidinyl-1'-yl]-methanone (765 mg, 53%) as a white foam, MS: m/e=537.2 (M+H$^+$).

(3RS,3'RS,4SR)- and (3RS,3'SR,4SR)-(3,5-Bis-trifluoromethyl-phenyl)-[3-chloro-3'-(4-fluoro-phenyl)-[1,4']bipiperidinyl-1'-yl]-methanone (696 mg, 1.30 mmol) was dissolved in N,N-dimethylformamide (15 mL) and sodium azide (505 mg, 7.79 mmol) was added at room temperature. The reaction mixture was stirred at 95° C. overnight and than diluted with 50 mL water. The mixture was extracted three times with 50 mL tert.-butyl-methyl ether. Organic phases were pooled, dried with magnesium sulfate and evaporated. The crude azide (704 mg, 100%) was used for the next steps without further purification.

The intermediate azide (704 mg, 1.30 mmol) was dissolved in methanol (50 mL) and palladium on charcoal (10%, 138 mg) was added. After stirring in a hydrogen atmosphere (1 bar) at room temperature overnight the mixture was filtered and the solvent was evaporated. The crude amine (490 mg, 73%) was used for the next step without further purification.

The intermediate amine (163 mg, 0.315 mmol) was dissolved in dichloromethane (5 mL) and triethylamine (0.132 mL, 0.945 mmol) and cyclopropane carboxylic acid chloride (0.035 mL, 0.378 mmol) were added at room temperature. The solvent was evaporated and flash chromatography on silica gel with cyclohexane/ethyl acetate/triethylamine 10:10:1 gave (3RS,3'RS,4SR)- and (3RS,3'SR,4SR)-(cyclopropanecarboxylic acid [1'-(3,5-bis-trifluoromethyl-benzoyl)-3'-(4-fluoro-phenyl)-[1,4']bipiperidinyl-3-yl]-amide (95 mg, 52%) as a light yellow foam, MS: m/e=586.1 (M+H$^+$).

EXAMPLE 78

(3RS,3'RS,4SR)- and (3RS,3'SR,4SR)-N-[1'-(3,5-Bis-trifluoromethyl-benzoyl)-3'-(4-fluoro-phenyl)-[1,4']bipiperidinyl-3-yl]-benzamide The title compound, MS: m/e=622.1 (M+H$^+$), was prepared in accordance with the general method of example 77 from the intermediate crude amine and benzoyl chloride.

EXAMPLE 79

(3RS,3'RS,4SR)- and (3RS,3'SR,4SR)-N-[1'-(3,5-Bis-trifluoromethyl-benzoyl)-3'-(4-fluoro-phenyl)-[1,4']bipiperidinyl-3-yl]-2-phenyl-acetamide The title compound, MS: m/e=636.2 (M+H$^+$), was prepared in accordance with the general method of example 77 from the intermediate crude amine and phenylacetyl chloride.

EXAMPLE 80

(−)-(3,5-Bis-trifluoromethyl-phenyl)-[3-(4-chloro-phenyl)-4-pyrrolidin-1-yl-piperidin-1-yl]-methanone Rac-cis-(3,5-Bis-trifluoromethyl-phenyl)-[3-(4-chloro-phenyl)-4-pyrrolidin-1-yl-piperidin-1-yl]-methanone was separated on Chiralpak AD® available from Merck Eurolab with 5% ethanol in heptane. The second fraction contained the more active enantiomer, $[\alpha]_{589}^{20}$=−42.97, $[\alpha]_{546}^{20}$=−51.90, $[\alpha]_{436}^{20}$=−100.61, $[\alpha]_{365}^{°}$=−189.94 (HCl-salt, c=0.4702, methanol).

EXAMPLE 81

Rac-cis-1-{4-[1-(3,5-Bis-trifluoromethyl-benzoyl)-3-(4-fluoro-phenyl)-piperidin-4-yl]-piperazin-1-yl}-2,2,2-trifluoro-ethanone The title compound, MS: m/e=600.0 (M+H$^+$), was prepared in accordance with the general method of example 32 from 1-benzyl-3-(4-fluoro-phenyl)-piperidin-4-one, piperazine and 3,5-bistrifluoromethyl-benzoyl chloride.

EXAMPLE 82

Rac-cis-(3,5-Bis-trifluoromethyl-phenyl)-[3-(4-fluoro-phenyl)-4-piperazin-1-yl-piperidin-1-yl]-methanone The title compound, MS: m/e=504.3 (M+H$^+$), was prepared in accordance with the general method of example 34 from rac-cis-1-{4-[1-(3,5-bis-trifluoromethyl-benzoyl)-3-(4-fluoro-phenyl)-piperidin-4-yl]-piperazin-1-yl}-2,2,2-trifluoro-ethanone.

EXAMPLE 83

Rac-cis-(3,5-Bis-trifluoromethyl-phenyl)-{3-(4-fluoro-phenyl)-4-[4-(2,2,2-trifluoro-ethyl)-piperazin-1-yl]-piperidin-1-yl}-methanone The title compound, MS: m/e=586.1 (M+H$^+$), was obtained as a by-product of rac-cis-1-{4-[1-(3,5-bis-trifluoromethyl-benzoyl)-3-(4-fluoro-phenyl)-piperidin-4-yl]-piperazin-1-yl}-2,2,2-trifluoro-ethanone (example 81).

EXAMPLE 84

Rac-cis-(3,5-Bis-trifluoromethyl-phenyl)-[4-(4-cyclopropanecarbonyl-piperazin-1-yl)-3-(4-fluoro-phenyl)-piperidin-1-yl]-methanone The title compound, MS: m/e=572.1 (M+H$^+$), was prepared in accordance with the general method of example 38 from rac-cis-(3,5-bis-trifluoromethyl-phenyl)-[3-(4-fluoro-phenyl)-4-piperazin-1-yl-piperidin-1-yl]-methanone and cyclopropane carboxylic acid chloride.

EXAMPLE 85

(+)-(3,5-Bis-trifluoromethyl-phenyl)-[4-(4-cyclopropanecarbonyl-piperazin-1-yl)-3-(4-fluoro-phenyl)-piperidin-1-yl]-methanone Rac-cis-(3,5-Bis-trifluoromethyl-phenyl)-[4-(4-cyclopropanecarbonyl-piperazin-1-yl)-3-(4-fluoro-phenyl)-piperidin-1-yl]-methanone was separated on Chiralpak AD® available from Merck Eurolab with 10% ethanol in heptane. The second fraction contained the more active enantiomer, $[\alpha]_{589}^{20}$=+14.52 (c=0.4615, methanol).

EXAMPLE 86

Rac-cis-(3,5-Bis-trifluoromethyl-phenyl)-[3-phenyl-4-(4-pyridin-2-yl-piperazin-1-yl)-piperidin-1-yl]-methanone The title compound, MS: m/e=563.3 (M+H$^+$), was prepared in accordance with the general method of example 59 from rac-cis-(3,5-bis-trifluoromethyl-phenyl)-(3-phenyl-4-piperazin-1-yl-piperidin-1-yl)-methanone and 2-chloropyridine.

EXAMPLE 87

Rac-cis-(3,5-Bis-trifluoromethyl-phenyl)-[3-(3,4-dichloro-phenyl)-4-morpholin-4-yl-piperidin-1-yl]-methanone The title compound, MS: m/e=555.1 (M+H$^+$), was prepared in accordance with the general method of example 26 from 1-benzyl-3-(3,4-dichloro-phenyl)-piperidin-4-one, morpholine and 3,5-bistrifluoromethyl-benzoyl chloride.

EXAMPLE 88

Rac-cis-(3,5-Bis-trifluoromethyl-phenyl)-[4-(4-cyclopropylmethyl-piperazin-1-yl)-3-(4-fluoro-phenyl)-piperidin-1-yl]-methanone The title compound, MS: m/e=558.3 (M+H$^+$), was prepared in accordance with the general method of example 35 from rac-cis-(3,5-bis-trifluoromethyl-phenyl)-[3-(4-fluoro-phenyl)-4-piperazin-1-yl-piperidin-1-yl]-methanone and bromomethyl cyclopropane.

EXAMPLE 89

Rac-cis-(3,5-Bis-trifluoromethyl-phenyl)-[3-(4-chloro-3-fluoro-phenyl)-4-morpholin-4-yl-piperidin-1-yl]-methanone The title compound, MS: m/e=539.3 (M+H$^+$), was prepared in accordance with the general method of example 26 from 1-benzyl-3-(4-chloro-3-fluoro-phenyl)-piperidin-4-one, morpholine and 3,5-bistrifluoromethyl-benzoyl chloride.

EXAMPLE 90

(−)-(3,5-Bis-trifluoromethyl-phenyl)-[3-(4-fluoro-phenyl)-4-(4-methyl-piperazin-1-yl)-piperidin-1-yl]-methanone Rac-cis)-(3,5-Bis-trifluoromethyl-phenyl)-[3-(4-fluoro-phenyl)-4-(4-methyl-piperazin-1-yl)-piperidin-1-yl]-methanone was separated on Chiralpak AD® available from Merck Eurolab with 5% isopropanol in heptane. The first fraction contained the more active enantiomer, $[\alpha]_{589}^{20}=-11.70$ (c=0.3846, chloroform).

EXAMPLE 91

Rac-cis-(3,5-Bis-trifluoromethyl-phenyl)-[3-(4-chloro-phenyl)-4-thiomorpholin-4-yl-piperidin-1-yl]-methanone The title compound, MS: m/e=537.2 (M+H$^+$), was prepared in accordance with the general method of example 26 from 1-benzyl-3-(4-chloro-phenyl)-piperidin-4-one, thiomorpholine and 3,5-bistrifluoromethyl-benzoyl chloride.

EXAMPLE 92

(−)-(3,5-Bis-trifluoromethyl-phenyl)-[3-phenyl-4-(4-methyl-piperazin-1-yl)-piperidin-1-yl]-methanone Rac-cis)-(3,5-Bis-trifluoromethyl-phenyl)-[3-phenyl-4-(4-methyl-piperazin-1-yl)-piperidin-1-yl]-methanone was separated on Chiralpak AD® available from Merck Eurolab with 4% isopropanol in heptane. The first fraction contained the more active enantiomer, $[\alpha]_{589}^{20}=-11.55$ (c=0.3291, chloroform).

EXAMPLE 93

Rac-cis-(3,5-Bis-trifluoromethyl-phenyl)-[3'-(4-chloro-phenyl)-4,4-difluoro-[1,4']bipiperidinyl-1'-yl]-methanone The title compound, MS: m/e=555.1 (M+H$^+$), was prepared in accordance with the general method of example 57 from rac-cis-1'-(3,5-bis-trifluoromethyl-benzoyl)-3'-(4-chloro-phenyl)-[1,4']bipiperidinyl-4-one and diethylamino sulfurtrifluoride.

EXAMPLE 94

Rac-cis-(3,5-Bis-trifluoromethyl-phenyl)-[3-(4-chloro-phenyl)-4-(1,1-dioxo-1l6-thiomorpholin-4-yl)-piperidin-1-yl]-methanone The title compound, MS: m/e=569.1 (M+H$^+$), was prepared in accordance with the general method of example 51 from rac-cis-(3,5-bis-trifluoromethyl-phenyl)-[3-(4-chloro-phenyl)-4-thiomorpholin-4-yl-piperidin-1-yl]-methanone and potassium peroxymonosulfate (Oxone®, available from E. I. duPont de Neumors, Wilmington, Del.).

EXAMPLE 95

Rac-cis-(3,5-Bis-trifluoromethyl-phenyl)-[3-(3,4-dichloro-phenyl)-4-thiomorpholin-4-yl-piperidin-1-yl]-methanone The title compound, MS: m/e=571.0 (M+H$^+$), was prepared in accordance with the general method of example 26 from 1-benzyl-3-(3,4-dichloro-phenyl)-piperidin-4-one, thiomorpholine and 3,5-bistrifluoromethyl-benzoyl chloride.

EXAMPLE 96

Rac-cis-(3,5-Bis-trifluoromethyl-phenyl)-[3-(4-methyl-phenyl)-4-thiomorpholin-4-yl-piperidin-1-yl]-methanone The title compound, MS: m/e=517.3 (M+H$^+$), was prepared in accordance with the general method of example 26 from 1-benzyl-3-(4-methyl-phenyl)-piperidin-4-one, thiomorpholine and 3,5-bistrifluoromethyl-benzoyl chloride.

EXAMPLE 97

Rac-cis-(3,5-Bis-trifluoromethyl-phenyl)-[3-(3,4-dichloro-phenyl)-4-(1,1-dioxo-1l 6-thiomorpholin-4-yl)-piperidin-1-yl]-methanone The title compound, MS: m/e=602.1 (M$^+$), was prepared in accordance with the general method of example 51 from rac-cis-(3,5-bis-trifluoromethyl-phenyl)-[3-(3,4-dichloro-phenyl)-4-thiomorpholin-4-yl-piperidin-1-yl]-methanone and potassium peroxymonosulfate (Oxone®).

EXAMPLE 98

Rac-cis-(3,5-Bis-trifluoromethyl-phenyl)-[3-(4-methyl-phenyl)-4-(1,1-dioxo-1l 6-thiomorpholin-4-yl)-piperidin-1-yl]-methanone The title compound, MS: m/e=549.2 (M$^+$), was prepared in accordance with the general method of example 51 from rac-cis-(3,5-bis-trifluoromethyl-phenyl)-[3-(4-methyl-phenyl)-4-thiomorpholin-4-yl-piperidin-1-yl]-methanone and potassium peroxymonosulfate (Oxone®).

EXAMPLE 99

Rac-cis-(3,5-Bis-trifluoromethyl-phenyl)-[4-(2,6-dimethyl-morpholin-4-yl)-3-p-tolyl-piperidin-1-yl]-methanone The title compound, MS: m/e=529.3 (M+H$^+$), was prepared in accordance with the general method of example 26 from 1-benzyl-3-(4-methyl-phenyl)-piperidin-4-one, cis-2,6-dimethyl-morpholine and 3,5-bistrifluoromethyl-benzoyl chloride.

EXAMPLE 100

(−)-{4-[1-(3,5-Bis-trifluoromethyl-benzoyl)-3-p-tolyl-piperidin-4-yl]-piperazin-1-yl}-2,2,2-trifluoro-ethanone Rac-cis-(1-{4-[1-(3,5-Bis-trifluoromethyl-benzoyl)-3-p-tolyl-piperidin-4-yl]-piperazin-1-yl}-2,2,2-trifluoro-ethanone (prepared in accordance with the general method of example 32 from 1-benzyl-3-(4-methyl-phenyl)-piperidin-4-one, piperazine and 3,5-bistrifluoromethyl-benzoyl chloride) was separated on Chiralpak AD® available from Merck Eurolab with 10% isopropanol in heptane. The first fraction contained the more active enantiomer, $[\alpha]_{589}^{20}=-6.63$, $[\alpha]_{546}^{20}=-8.10$, $[\alpha]_{436}^{20}=-22.10$, $[\alpha]_{365}^{20}=-61.87$ (c=0.1358, methanol).

EXAMPLE 101

(−)-4-[1-(3,5-Bis-trifluoromethyl-benzoyl)-3-phenyl-piperidin-4-yl]-piperazine-1-carboxylic Acid Tert-Butyl Ester Rac-cis-4-[1-(3,5-Bis-trifluoromethyl-benzoyl)-3-phenyl-piperidin-4-yl]-piperazine-1-carboxylic acid tert-butyl ester (prepared from rac-cis-(3,5-bis-trifluoromethyl-phenyl)-(3-phenyl-4-piperazin-1-yl-piperidin-1-yl)-methanone and di-tert.-butyl-carbonat) was separated on Chiralpak AD® available from Merck Eurolab with 6% isopropanol in heptane. The first fraction contained the more active enantiomer, $[\alpha]_{589}^{20}=-2.23$ (c=0.6740, chloroform).

EXAMPLE 102

(−)-4-(3,5-Bis-trifluoromethyl-phenyl)-[4-(4-cyclopropylmethyl-piperazin-1-yl)-3-p-tolyl-piperidin-1-yl]-methanone (−)-(1-{4-[1-(3,5-Bis-trifluoromethyl-benzoyl)-3-p-tolyl-piperidin-4-yl]-piperazin-1-yl}-2,2,2-trifluoro-ethanone (245 mg, 0.411 mmol) was dissolved in methanol (1.5 mL). Water (0.15 mL) and potassium carbonate (170 mg, 123 mmol) were added and the reaction mixture was stirred at room temperature for 3 hours. Water (10 mL) was added and the mixture was extracted three times with 20 mL dichloromethane. Organic phases were pooled, dried with magnesium sulfate and evaporated.

The intermediate free piperazine was dissolved in N,N-dimethylformamide (10 mL) and potassium carbonate (166 mg, 1.20 mmol) and bromomethylcyclopropane (0.043 mL, 0.440 mmol) were added at room temperature. The reaction mixture was stirred at room temperature for 3 hours. Water (30 mL) was added and the mixture was extracted three times with 50 mL tert-butyl methylether. Organic phases were pooled, dried with magnesium sulfate and evaporated. Flash chromatography on silica gel with cyclohexane/ethyl acetate/triethylamine 30:10:1 gave the title compound (171 mg, 77%) as an off-white solid, MS: m/e=554.3 (M+H$^+$), $[\alpha]_{589}^{20}=-19.81$ (c=0.4089, chloroform).

EXAMPLE 103

(−)-(3,5-Bis-trifluoromethyl-phenyl)-[4-(4-cyclopropanecarbonyl-piperazin-1-yl)-3-p-tolyl-piperidin-1-yl]-methanone The title compound, MS: m/e=568.3 (M+H$^+$), $[\alpha]_{589}^{20}=-6.48$ (c=0.4012, chloroform), was prepared in accordance with the general method of example 102 (part1) and example 38 from (−)-(1-{4-[1-(3,5-bis-trifluoromethyl-benzoyl)-3-p-tolyl-piperidin-4-yl]-piperazin-1-yl}-2,2,2-trifluoro-ethanone and cyclopropyl carbonyl chloride.

EXAMPLE 104

(−)-(3,5-Bis-trifluoromethyl-phenyl)-{4-[4-(morpholine-4-carbonyl)-piperazin-1-yl]-3-p-tolyl-piperidin-1-yl}-methanone The title compound, MS: m/e=613.2 (M+H$^+$), $[\alpha]_{589}^{20}=-10.99$ (c=0.4369, chloroform), was prepared in accordance with the general method of example 102 (part1) and example 38 from (−)-(1-{4-[1-(3,5-bis-trifluoromethyl-benzoyl)-3-p-tolyl-piperidin-4-yl]-piperazin-1-yl}-2,2,2-trifluoro-ethanone and 4-morpholine carbonyl chloride.

EXAMPLE 105

(−)-(3,5-Bis-trifluoromethyl-phenyl)-[4-(4-methanesulfonyl-piperazin-1-yl)-3-p-tolyl-piperidin-1-yl]-methanone The title compound, MS: m/e=578.1 (M+H$^+$), $[\alpha]_{589}^{20}=-19.14$ (c=0.4545, chloroform), was prepared in accordance with the general method of example 102 (part1) and example 38 from (−)-(1-{4-[1-(3,5-bis-trifluoromethyl-benzoyl)-3-p-tolyl-piperidin-4-yl]-piperazin-1-yl}-2,2,2-trifluoro-ethanone and methane sulfonyl chloride.

EXAMPLE 106

Rac-cis-1-{4-[1-(3,5-Bis-trifluoromethyl-benzoyl)-3-(4-chloro-phenyl)-piperidin-4-yl]-piperazin-1-yl}-2,2,2-trifluoro-ethanone To a mixture of 1-benzyl-3-(4-chloro-phenyl)-piperidin-4-one (15.2 g, 38.5 mmol) and piperazine (6.78 g, 77.1 mmol) in ethanol (6 mL) was added tetraisopropyl-orthotitanate (22.8 mL, 77.1 mmol) at room temperature. After stirring at room temperature for 3 days the reaction mixture was diluted with ethanol (250 mL) and sodium cyanoborohydride (5.10 g, 77.1 mmol) was added. The reaction mixture was stirred at room temperature for 24 h and was diluted with water (30 mL). The inorganic precipitate was filtered off and washed with ethanol and dichloromethane. The solvent was evaporated and the residue was taken up in ethylenglycol (100 mL) and sodium hydroxide (3.08 g, 77.1 mmol) was added. The reaction mixture was stirred at 130° C. for 15 min. After cooling water (200 mL) was added and the mixture was extracted four times with 200 mL tert.-butyl methyl ether. Organic phases were pooled, dried with magnesium sulfate and evaporated. Flash chromatography on silica gel with methylene chloride/methanol/triethyl amine 98:1:1 gave rac-cis-1-[1-benzyl-3-(4-chloro-phenyl)-piperidin-4-yl]-piperazine (9.54 g, 67%) as a yellow oil, MS: m/e=336.3 (M+H$^+$).

Rac-cis-1-[1-Benzyl-3-(4-chloro-phenyl)-piperidin-4-yl]-piperazine (2.00 g, 5.41 mmol) was dissolved in dichloromethane (130 mL) and 9-fluorenylmethyl-chloroformate (1.71 g, 6.49 mmol) in dichloromethane (50 mL) was added at 0° C. The reaction mixture was stirred at room temperature overnight and diluted with sat sodium bicarbonate solution (100 mL). The organic phase was separated and the aqueous layer was extracted twice with 150 mL dichloromethane. Organic phases were pooled, dried with magnesium sulfate and evaporated. Flash chromatography on silica gel with cyclohexane/ethyl acetate 6:1 gave rac-cis-4-[1- benzyl-3-(4-chloro-phenyl)-piperidin-4-yl]-piperazine-1-carboxylic acid 9H-fluoren-9-ylmethyl ester (1.75 g, 55%) as a light yellow solid, MS: m/e=592.3 (M+).

Rac-cis-4-[1-Benzyl-3-(4-chloro-phenyl)-piperidin-4-yl]-piperazine-1-carboxylic acid 9H-fluoren-9-ylmethyl ester (1.68 g, 2.84 mmol) was dissolved in toluene (60 mL) and 1-chloroethyl-chloroformate (0.348 mL, 3.13 mmol) were added. The reaction mixture was refluxed overnight. Methanol (55 mL) was added and reflux was continued for 4 h. The solvents were evaporated. The crude intermediate was dissolved in dichloromethane (50 mL) and triethylamine (1.99 mL, 14.2 mmol) and 3,5-bistrifluoromethyl-benzoyl chloride (0.643 mL, 3.55 mmol) were added. The reaction mixture was stirred at room temperature overnight and than diluted with 50 mL water. The organic phase was separated and the aqueous layer was extracted twice with 50 mL dichloromethane. Organic phases were pooled, dried with magnesium sulfate and evaporated. Flash chromatography on silica gel with cyclohexane/ethyl acetate 1:1 gave rac-cis-4-[1-(3,5-bis-trifluoromethyl-benzoyl)-3-(4-chloro-phenyl)-piperidin-4-yl]-piperazine-1-carboxylic acid 9H-fluoren-9-ylmethyl ester (1.84 g, 87%) as an off-white solid, MS: m/e=742.3 (M+H+).

Rac-cis-4-[1-(3,5-Bis-trifluoromethyl-benzoyl)-3-(4-chloro-phenyl)-piperidin-4-yl]-piperazine-1-carboxylic acid 9H-fluoren-9-ylmethyl ester (1.79 g, 2.42 mmol) was dissolved in dichloromethane (24 mL). Piperidine (2.4 mL) was added and the reaction mixture was stirred at room temperature overnight. The solvent and the piperidine were evaporated. The crude intermediate was dissolved in dichloromethane (25 mL). 4-Dimethylamino-pyridine (6 mg, 0.05 mmol), pyridine (0.488 mL, 6.04 mmol) and trifluoroacetic acid anhydride (2.6 mL, 18.2 mmol) were added. The reaction mixture was stirred at room temperature overnight and than diluted with 1N sodium hydroxide solution (25 mL). The organic phase was separated and the aqueous layer was extracted twice with 50 mL dichloromethane. Organic phases were pooled, dried with magnesium sulfate and evaporated. Flash chromatography on silica gel with cyclohexane/ethyl acetate 1:2 gave rac-cis-1-{4-[1-(3,5-bis-trifluoromethyl-benzoyl)-3-(4-chloro-phenyl)-piperidin-4-yl]-piperazin-1-yl}-2,2,2-trifluoro-ethanone (730 mg, 49%) as an off-white solid, MS: m/e=616.2 (M+H+).

EXAMPLE 107

Rac-cis-(3,5-bis-trifluoromethyl-phenyl)-[3'-(4-chloro-phenyl)-4-dimethylamino-[1,4']bipiperidinyl-1'-yl]-methanone To a 2 M solution of dimethylamine in methanol (0.38 mL, 0.75 mmol) was added titanium(IV) isopropoxide (0.11 mL, 0.38 mmol) at room temperature. After 10 min. a solution of 1'-(3,5-bis-trifluoromethyl-benzoyl)-3'-(4-chloro-phenyl)-[1,4']bipiperidinyl-4-one (0.10 g, 0.19 mmol) in 1 mL methanol was added to the resulting suspension. The reaction mixture was stirred at room temperature for 5 h. Sodium borohydride (7.0 mg, 0.19 mmol) was added, and stirring at room temperature was continued over night. After quenching with water (0.5 mL) and dilution with methanol (1 ml) the suspension was filtered. The filtrate was concentrated and the resulting slurry triturated with several batches of dichloromethane. The combined organic layers were concentrated. Flash column chromatography afforded the title compound as an off-white solid (58 mg, 55%), MS: m/e=562 (M+H+).

EXAMPLE 108

(−)-1-{4-[1-(3,5-Bis-trifluoromethyl-benzoyl)-3-(4-chloro-phenyl)-piperidin-4-yl]-piperazin-1-yl}-2,2,2-trifluoro-ethanone Rac-cis-1-{4-[1-(3,5-Bis-trifluoromethyl-benzoyl)-3-(4-chloro-phenyl)-piperidin-4-yl]-piperazin-1-yl}-2,2,2-trifluoro-ethanone was separated on Chiralpak AD® available from Merck Eurolab with 8% isopropanol in heptane. The first fraction contained the more active enantiomer, $[\alpha]_{589}^{20}$=−19.32 (c 0.5020, chloroform).

EXAMPLE 109

Rac-cis-(3,5-Bis-trifluoromethyl-phenyl)-[3'-(4-chloro-phenyl)-4-morpholin-4-yl-[1,4']bipiperidinyl-1'-yl]-methanone To a solution of morpholine (0.065 mL, 0.75 mmol) in 1 mL methanol was added titanium(IV) isopropoxide (0.11 mL, 0.38 mmol) at room temperature. After 20 min. 1'-(3, 5-bis-trifluoromethyl-benzoyl)-3'-(4-chloro-phenyl)-[1,4'] bipiperidinyl-4-one (0.10 g, 0.19 mmol) was added to the resulting suspension. The reaction mixture was stirred at room temperature for 5 h. Sodium borohydride (7.0 mg, 0.19 mmol) was added, and stirring at room temperature was continued over night. After quenching with water (0.5 mL) the suspension was triturated with several batches of dichloromethane. The combined organic layers were filtered and concentrated. Flash column chromatography afforded the title compound as a white solid (72 mg, 64%), MS: m/e=604 (M+H+).

EXAMPLE 110

(−)-(3,5-Bis-trifluoromethyl-phenyl)-[4-(4-cyclopropyl-piperazin-1-yl)-3-p-tolyl-piperidin-1-yl]-methanone (−)-(1-{4-[1-(3,5-Bis-trifluoromethyl-benzoyl)-3-p-tolyl-piperidin-4-yl]-piperazin-1-yl}-2,2,2-trifluoro-ethanone (245 mg, 0.411 mmol) was dissolved in methanol (1.5 mL). Water (0.15 mL) and potassium carbonate (170 mg, 123 mmol) were added and the reaction mixture was stirred at room temperature for 3 hours. Water (10 mL) was added and the mixture was extracted three times with 20 mL dichloromethane. Organic phases were pooled, dried with magnesium sulfate and evaporated.

The intermediate free piperazine was dissolved in methanol (10 mL) and acetic acid (0.109 mL, 1.90 mmol), powdered molecular sieves (1 small spatula), [(1-ethoxycyclopropyl)oxy]trimethylsilane (0.152 mL, 0.761 mmol) and sodium cyanoborohydride (36 mg, 0.571 mmol) were added. The reaction mixture refluxed for 8 hours, cooled and filtered. 2N Sodium hydroxide solution (20 mL) was added to the filtrate and the mixture was extracted three times with 50 mL ethyl acetate. Organic phases were pooled, dried with magnesium sulfate and evaporated. Chromatography on silica gel with dichloromethane/triethylamine 99:1 gave the title compound (160 mg, 72%) as a white foam, MS: m/e=540.3 (M+H+), $[\alpha]_{589}^{20}$=−11.02, $[\alpha]_{546}^{20}$=−13.78, $[\alpha]_{436}^{20}$=−36.66, $[\alpha]_{365}^{20}$=−94.73 (c=0.4719, chloroform).

EXAMPLE 111

(−)-(3,5-Bis-trifluoromethyl-phenyl)-[4-(4-methyl-piperazin-1-yl)-3-p-tolyl-piperidin-1-yl]-methanone The title compound, MS: m/e=514.4 (M+H+), $[\alpha]_{589}^{20}$=−25.92, $[\alpha]_{546}^{20}$=−32.60, $[\alpha]_{436}^{20}$=−71.06, $[\alpha]_{365}^{20}$=−152.15 (c=0.1196, chloroform), was prepared in accordance with the general method of example 102 from (−)-(1-{4-[1-(3,5-bis-trifluoromethyl-benzoyl)-3-p-tolyl-piperidin-4-yl]-piperazin-1-yl}-2,2,2-trifluoro-ethanone and methyl iodide.

EXAMPLE 112

Rac-cis-(3,5-Bis-trifluoromethyl-phenyl)-[3'-(4-chloro-phenyl)-4-cydopropylamino-[1,4']bipiperidinyl-1'-yl]-methanone To a solution of cyclopropyl amine (0.014 mL, 0.21 mmol), 1'-(3,5-bis-trifluoromethyl-benzoyl)-3'-(4-chlorophenyl)-[1,4']bipiperidinyl-4-one (0.10 g, 0.19 mmol) and 1 drop of a concentrated aqueous solution of hydrochloric acid in 2 mL ethanol was heated at reflux for two hours. After cooling to 0° C. sodium borohydride (9.0 mg, 0.23 mmol) was added. The reaction mixture was allowed to warm to room temperature over night. After quenching with water (0.5 mL) the mixture was concentrated. Dissolution of the residue in dichloromethane was followed by washing with three portions of water, drying with sodium sulfate and concentration. Flash column chromatography afforded the title compound as a white solid (22 mg, 21%), MS: m/e=574 (M+H$^+$).

EXAMPLE 113

(−)-(3,5-Bis-trifluoromethyl-phenyl)-[3-(4-chloro-phenyl)-4-(4-cyclopropylmethyl-piperazin-1-yl)-piperidin-1-yl]-methanone The title compound, MS: m/e=574.1 (M+H$^+$), $[\alpha]_{589}^{20}$=−18.46, $[\alpha]_{546}^{20}$=−27.04, (c=0.3846, chloroform), was prepared in accordance with the general method of example 102 from (−)-1-{4-[1-(3,5-bis-trifluoromethyl-benzoyl)-3-(4-chloro-phenyl)-piperidin-4-yl]-piperazin-1-yl}-2,2,2-trifluoro-ethanone and cyclopropylmethylbromide.

EXAMPLE 114

(−)-(3,5-Bis-trifluoromethyl-phenyl)-[4-(4-cyclopropylmethyl-piperazin-1-yl)-3-phenyl-piperidin-1-yl]-methanone (−)-4-[1-(3,5-Bis-trifluoromethyl-benzoyl)-3-phenyl-piperidin-4-yl]-piperazine-1-carboxylic acid tert-butyl ester (244 mg, 0.417 mmol) was dissolved in dichloromethane (10 mL). Trifluoroacetic acid (0.638 mL, 8.33 mmol) was added and the reaction mixture was stirred at room temperature for 3 hours. Saturated sodium bicarbonate solution was added until pH 8 and the mixture was extracted three times with 30 mL dichloromethane. Organic phases were pooled, dried with magnesium sulfate and evaporated.

The intermediate free piperazine was dissolved in N,N-dimethylformamide (10 mL) and potassium carbonate (166 mg, 1.20 mmol) and bromomethylcyclopropane (0.043 mL, 0.440 mmol) were added at room temperature. The reaction mixture was stirred at room temperature for 3 hours. Water (30 mL) was added and the mixture was extracted three times with 50 mL tert-butyl methylether. Organic phases were pooled, dried with magnesium sulfate and evaporated. Flash chromatography on silica gel with cyclohexane/ethyl acetate/triethylamine 20:10:1 gave the title compound (100 mg, 44%) as a white solid, MS: m/e=540.3 (M+H$^+$), $[\alpha]_{589}^{20}$=−7.80, $[\alpha]_{546}^{20}$=−9.69, $[\alpha]_{436}^{20}$=−28.60, $[\alpha]_{365}^{20}$=−78.71 (c 0.4231, chloroform).

EXAMPLE 115

(−)-(3,5-Bis-trifluoromethyl-phenyl)-{4-[4-(2-hydroxy-ethyl)-piperazin-1-yl]-3-phenyl-piperidin-1-yl}-methanone The title compound, MS: m/e=530.3 (M+H$^+$), $[\alpha]_{589}^{20}$=−8.02, $[\alpha]_{546}^{20}$=−5.61, $[\alpha]_{436}^{20}$=−20.05, $[\alpha]_{365}^{20}$=−59.35 (c 0.1247, chloroform), was prepared in accordance with the general method of example 114 from (−)-4-[1-(3,5-bis-trifluoromethyl-benzoyl)-3-phenyl-piperidin-4-yl]-piperazine-1-carboxylic acid tert-butyl ester and 2-amino ethanol.

EXAMPLE 116

Rac-cis-(3,5-Dichloro-phenyl)-[4-(4-methyl-piperazin-1-yl)-3-phenyl-piperidin-1-yl]-methanone The title compound, MS: m/e=432.2 (M+H$^+$), was prepared in accordance with the general method of example 26 from 1-benzyl-3-phenyl-piperidin-4-one, N-methyl-piperazine and 3,5-dichloro-benzoyl chloride.

EXAMPLE 117

(−)-(3,5-Bis-trifluoromethyl-phenyl)-[4-(4-phenyl-piperazin-1-yl)-3-p-tolyl-piperidin-1-yl]-methanone (−)-(1-{4-[1-(3,5-Bis-trifluoromethyl-benzoyl)-3-p-tolyl-piperidin-4-yl]-piperazin-1-yl}-2,2,2-trifluoro-ethanone (245 mg, 0.411 mmol) was dissolved in methanol (1.5 mL). Water (0.15 mL) and potassium carbonate (170 mg, 123 mmol) were added and the reaction mixture was stirred at room temperature for 3 hours. Water (10 mL) was added and the mixture was extracted three times with 20 mL dichloromethane. Organic phases were pooled, dried with magnesium sulfate and evaporated.

The intermediate free piperazine was dissolved in toluene (5 mL) and bromobenzene (0.084 mL, 0.80 mmol), sodium tert.-butylate (54 mg, 0.561 mmol), tris(dibenzylidenaceton) dipalladium (4 mg, 0.004 mmol) and rac-2,2'-bis (diphenylphosphino)-1,1'-binaphthyl (5 mg, 0.008 mmol) were added. The reaction mixture was stirred at 80° C. overnight. Water (20 mL) was added and the mixture was extracted three times with 20 mL ethyl acetate. Organic phases were pooled, dried with magnesium sulfate and evaporated. Chromatography on silica gel with dichloromethane/triethylamine 99:1 gave the title compound (128 mg, 54%) as an yellow oil, MS: m/e=576.1 (M+H$^+$), $[\alpha]_{589}^{20}$=−10.62, $[\alpha]_{546}^{20}$=−9.66, $[\alpha]_{436}^{20}$=−20.28 (c=0.1035, chloroform).

EXAMPLE 118

(3RS,3'RS,4SR)- and (3RS,3'SR,4SR)-[4-(3-Amino-pyrrolidin-1-yl)-3-(4-fluoro-phenyl)-piperidin-1-yl]-(3,5-bis-trifluoromethyl-phenyl)-methanone The title compound, MS: m/e=504.3 (M+H$^+$), was prepared in accordance with the general method of example 77, step 1–3, from (3R,3'R,4S)- and (3S,3'R,4R)-(3,5-bis-trifluoromethyl-phenyl)-[3-(4-fluoro-phenyl)-4-(3-hydroxy-pyrrolidin-1-yl)-piperidin-1-yl]-methanone. The 3'-stereogenic center racemized under the reaction conditions.

EXAMPLE 119

(−)-(3,5-Bis-trifluoromethyl-phenyl)-[4-(4-cyclopropyl-piperazin-1-yl)-3-phenyl-piperidin-1-yl]-methanone The title compound, MS: m/e=526.2 (M+H$^+$), $[\alpha]_{589}^{20}$=−6.17, $[\alpha]_{436}^{20}$=−23.81, $[\alpha]_{365}^{20}$=−74.09 (c=0.1134, chloroform), was prepared in accordance with the general method of example 114 (step1) and example 110 (step 2) from (3S,4R) or (3R,4S)-4-[1-(3,5-bis-trifluoromethyl-benzoyl)-3-phenyl-piperidin-4-yl]-piperazine-1-carboxylic acid tert-butyl ester and [(1-ethoxycyclopropyl)-oxy] trimethylsilane.

EXAMPLE 120

Rac-cis-(3,5-Difluoro-phenyl)-[4-(4-methyl-piperazin-1-yl)-3-phenyl-piperidin-1-yl]-methanone The title compound, MS: m/e=400.5 (M+H$^+$), was prepared in accordance with the general method of example 26 from 1-benzyl-3-phenyl-piperidin-4-one, N-methyl-piperazine and 3,5-difluoro-benzoyl chloride.

EXAMPLE 121

(3RS,3'RS,4SR)- and (3RS,3'SR,4SR)-
[Cyclopropanecarboxylic acid {1-1-(3,5-bis-
trifluoromethyl-benzoyl)-3-(4-fluoro-phenyl)-
piperidin-4-yl]-pyrrolidin-3-yl}-amide The title compound, MS: m/e=572.2 (M+H$^+$), was prepared in accordance with the general method of example 38 from (3RS,3'RS,4SR)- and (3RS,3'SR,4SR)-[4-(3-amino-pyrrolidin-1-yl)-3-(4-fluoro-phenyl)-piperidin-1-yl]-(3,5-bis-trifluoromethyl-phenyl)-methanone and cyclopropane carboxylic acid chloride.

EXAMPLE 122

(3RS,3'RS,4SR)- and (3RS,3'SR,4SR)-
[Cyclopropanecarboxylic acid {1-1-(3,5-bis-
trifluoromethyl-benzoyl)-3-(4-fluoro-phenyl)-
piperidin-4-yl]-pyrrolidin-3-yl}-methyl-amide (3RS,3'RS,4SR)- and (3RS,3'SR,4SR)-[Cyclopropanecarboxylic acid {1-[1-(3,5-bis-trifluoromethyl-benzoyl)-3-(4-fluoro-phenyl)-piperidin-4-yl]-pyrrolidin-3-yl}-amide (155 mg, 0.271 mmol) was dissolved in N,N-dimethylforamide (5 mL). Sodium hydride (17 mg, 55% in mineral oil, 0.407 mmol) and methyl iodide (0.021 mL, 0.339 mmol) were added and the reaction mixture was stirred at room temperature overnight. Water (30 mL) was added and the mixture was extracted three times with 50 mL tert.-butyl methyl ether. Organic phases were pooled, dried with magnesium sulfate and evaporated. Chromatography on silica gel with methylen chloride/triethyl amine 99:1 gave the desired product (30 mg, 19%) as a colorless oil, MS: m/e=586.2 (M+H$^+$).

EXAMPLE 123

(3RS,3'RS,4SR)- and (3RS,3'SR,4SR)-(3,5-Bis-
trifluoromethyl-phenyl)-[4-(3-dicyclopropylamino-
pyrrolidin-1-yl)-3-(4-fluoro-phenyl)-piperidin-1-yl]-
methanone The title compound, MS: m/e=584.3 (M+H)$^+$, was prepared in accordance with the general method of example 110 (step 2) from (3RS,3'RS,4SR)- and (3RS,3'SR,4SR)-[4-(3-amino-pyrrolidin-1-yl)-3-(4-fluoro-phenyl)-piperidin-1-yl]-(3,5-bis-trifluoromethyl-phenyl)-methanone and [(1-ethoxycyclopropyl)-oxy]trimethylsilane.

EXAMPLE 124

(3RS,3'RS,4SR)- and (3RS,3'SR,4SR)-[4-[3-(Bis-
cyclopropylmethyl-amino)-pyrrolidin-1-yl]-3-(4-
fluoro-phenyl)-piperidin-1-yl]-(3,5-bis-
trifluoromethyl-phenyl)-methanone The title compound, MS: m/e=612.2 (M+H)$^+$, was prepared in accordance with the general method of example 35 from (3RS,3'RS,4SR)- and (3RS,3'SR,4SR)-[4-(3-amino-pyrrolidin-1-yl)-3-(4-fluoro-phenyl)-piperidin-1-yl]-(3,5-bis-trifluoromethyl-phenyl)-methanone and bromomethyl cyclopropane.

EXAMPLE 125

(3RS,3'RS,4SR)- and (3RS,3'SR,4SR)-(3,5-Bis-
trifluoromethyl-phenyl)-[4-(3-dimethylamino-
pyrrolidin-1-yl)-3-(4-fluoro-phenyl)-piperidin-1-yl]-
methanone (3RS,3'RS,4SR)- and (3RS,3'SR,4SR)-[4-(3-Amino-pyrrolidin-1-yl)-3-(4-fluoro-phenyl)-piperidin-1-yl]-(3,5-bis-trifluoromethyl-phenyl)-methanone (200 mg, 0.397 mmol) was dissolved in formic acid (2 mL) and formaldehyd (0.094 mL, 36% solution in water, 1.19 mmol) was added. The reaction mixture was stirred at 110° C. overnight. Saturated sodium bicarbonate solution was added until pH 9 and the mixture was extracted three times with 50 mL ethyl acetate. Organic phases were pooled, dried with magnesium sulfate and evaporated. Flash chromatography on silica gel with methanol in methylen chloride (0%–10% gradient) gave the title product (150 mg, 71%) as an off-white foam, MS: m/e=532.2 (M+H$^+$).

EXAMPLE 126

(−)-(3,5-Bis-trifluoromethyl-phenyl)-[4-(4-
cyclopropanecarbonyl-piperazin-1-yl)-3-(4-chloro-
phenyl)-piperidin-1-yl]-methanone The title compound, MS: m/e=588.2 (M+H$^+$), $[\alpha]_{589}^{20}$=−16.03, $[\alpha]_{546}^{20}$=−20.15, $[\alpha]_{436}^{20}$=−45.28, $[\alpha]_{365}^{20}$=−102.27 (c=0.4615, chloroform), was prepared in accordance with the general method of example 102 (part1) and example 38 from (−)-(1-{4-[1-(3,5-bis-trifluoromethyl-benzyl)-3-(4-chloro-phenyl)-piperidin-4-yl piperazin-1-yl}-2,2,2-trifluoro-ethanone and cyclopropyl carbonyl chloride.

EXAMPLE 127

(+)-(3,5-Dichloro-phenyl)-[4-(4-methyl-piperazin-1-
yl)-3-phenyl-piperidin-1-yl]-methanone Rac-cis-(3,5-Dichloro-phenyl)-[4-(4-methyl-piperazin-1-yl)-3-phenyl-piperidin-1-yl]-methanone was separated on Chiralpak AD® available from Merck Eurolab with 10% isopropanol in heptane. The first fraction contained the more active enantiomer, $[\alpha]_{589}^{20}$=+23.46, $[\alpha]_{546}^{20}$=+27.81, $[\alpha]_{436}^{20}$=+39.10, $[\alpha]_{365}^{20}$=+38.23 (c=0.1151, methanol).

EXAMPLE 128

Rac-cis-(3-Fluoro-5-trifluoromethyl-phenyl)-[4-(4-
methyl-piperazin-1-yl)-3-phenyl-piperidin-1-yl]-
methanone The title compound, MS: m/e=450.5 (M+H$^+$), was prepared in accordance with the general method of example 26 from 1-benzyl-3-phenyl-piperidin-4-one, N-methyl-piperazine and 3-fluoro-5-trifluoromethyl-benzoyl chloride.

EXAMPLE 129

(−)-(3,5-Bis-trifluoromethyl-phenyl)-[3-(4-chloro-
phenyl)-4-(4-methyl-piperazin-1-yl)-piperidin-1-yl]-
methanone The title compound, MS: m/e=534.3 (M+H$^+$), $[\alpha]_{589}^{20}$=−53.04, $[\alpha]_{546}^{20}$=−65.78, $[\alpha]_{436}^{20}$=−135.72, $[\alpha]_{365}^{20}$=−277.94 (c=0.3846, chloroform), was prepared in accordance with the general methods of example 102 (part1) and example 125 from (−)-(1-{4-[1-(3,5-bis-trifluoromethyl-benzoyl)-3-(4-chloro-phenyl)-piperidin-4-yl]-piperazin-1-yl}-2,2,2-trifluoro-ethanone and formaldehyde.

EXAMPLE 130

(−)-(3,5-Bis-trifluoromethyl-phenyl)-[3-(4-chloro-
phenyl)-4-(4-cyclopropyl-piperazin-1-yl)-piperidin-
1-yl]-methanone The title compound, MS: m/e=560.2 (M+H$^+$), $[\alpha]_{589}^{20}$=−24.38, $[\alpha]_{546}^{20}$=−30.39, $[\alpha]_{436}^{20}$=−64.51 (c=0.6154, chloroform), was prepared in accordance with the general methods of example 102 (step1) and example 110 (step2) from (−)-(1-{4-[1-(3,5-bis-trifluoromethyl-benzoyl)-3-(4-chloro-phenyl)-piperidin-4-yl]-piperazin-1-yl}-2,2,2-trifluoro-ethanone and [(1-ethoxycyclopropyl)-oxy] trimethylsilane.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

EXAMPLE D

An injection solution may have the following composition and is manufactured in usual manner:

| Active substance | 1.0 mg |
| --- | --- |
| 1 n HCl | 20.0 µl |
| acetic acid | 0.5 mg |
| NaCl | 8.0 mg |
| phenol | 10.0 mg |
| 1 n NaOH | q.s. ad pH 5 |
| H$_2$O | q.s. ad 1 ml |

What is claimed is:
1. A compound of formula

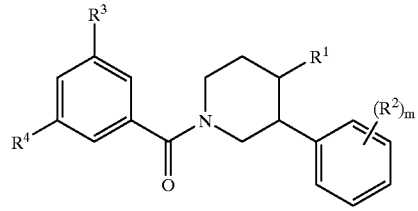

I wherein
$R^1$ a) is unsubstituted phenyl or phenyl substituted by at least one substituent selected from the group $R^{1'}$ consisting of
halogen,
trifluoromethyl,
unsubstituted piperazinyl or piperazinyl substituted by at least one substitutent selected from the group consisting of lower alkyl, -morpholinyl,
NH-phenyl,
pyrrolidinyl,
NH(CH$_2$)$_n$—O-lower alkyl,
NR$^a$R$^b$,
NH(CH$_2$)$_n$-cycloalkyl, and
NH(CH$_2$)$_n$-NR$^c$R$^d$, or is
b) unsubstituted morpholinyl or morpholinyl substituted by one or two lower alkyl groups, or is
c) unsubstituted piperazinyl or piperazinyl substituted in the 4-position by the group $R^{1''}$ which is selected from the group consisting of
lower alkyl,
cycloalkyl,
phenyl,
benzoxazolyl,
pyridinyl,
pyrimidinyl
pyrazinyl,
(CH$_2$)$_n$-cycloalkyl,
(CH$_2$)$_n$-phenyl,
(CH$_2$)$_n$-hydroxy,
(CH$_2$)$_n$—CF$_3$,
(CH$_2$)$_n$—C(O)-morpholinyl,
(CH$_2$)$_n$—C(O)—N(R$^e$)-unsubstituted phenyl, or —(CH$_2$)$_n$—C(O)—N(R$^e$)-phenyl substituted by lower alkyl or halogen,
(CH$_2$)$_n$—C(O)—NR$^f$R$^g$,
C(O)-unsubstituted phenyl or phenyl substituted by a substitutent selected from the group consisitng of
trifluoromethyl,
C(O)—(CH$_2$)$_n$-phenyl, C(O)—NR$^h$R$^i$,
C(O)—NR$^j$—(CHR$^k$)$_n$-phenyl,
C(O)-lower alkyl,
C(O)—CF$_3$,
C(O)-cycloalkyl,
C(O)-morpholinyl,
C(O)O-lower alkyl,
C(O)—O—(CH$_2$)$_n$-NR$^l$R$^m$ and
S(O)$_2$-lower alkyl,
or is
- d) unsubstituted pyrrolidinyl or pyrrolidinyl substituted by at least one group R$^{1'''}$, which is selected from the group consisting of
  halogen,
  hydroxy,
  =O,
  NR$^n$R$^o$,
  N(cycloalkyl)$_2$,
  N[(CH$_2$)$_n$cycloalkyl]$_2$,
  NR$^p$—C(O)-cycloalkyl and
  O—(CH$_2$)$_n$-cycloalkyl, or is
- e) unsubstituted piperidinyl or piperidinyl substituted by at least one group R$^{1''''}$ in the 3 or 4-position selected from the group consisting of
  hydroxy,
  =O,
  halogen,
  morpholinyl,
  NR$^q$R$^r$,
  NR$^s$-cycloalkyl,
  NR$^t$—C(O)-cycloalkyl,
  NR$^u$—C(O)-phenyl,
  NR$^v$—C(O)—(CH$_2$)$_n$-phenyl and
  O—(CH$_2$)$_n$-cycloalkyl,
or is
- f) thiomorpholinyl, 1-oxo-thiomorpholinyl or 1,1-dioxothiomorpholinyl;

R$^2$ is, independently, selected from the group consisting of hydrogen, halogen, lower alkyl, —NH—(CH$_2$)$_n$—O-lower alkyl pyrrolidinyl and morpholinyl;

R$^3$/R$^4$ are, independently from each other, trifluoromethyl or halogen;

R, R$^{a-v}$ are independently hydrogen or lower alkyl;

n is 1, 2, 3 or 4; and m is 0, 1 or 2;

or a pharmaceutically acceptable acid addition salt thereof.

2. The compound of claim 1 having the formula

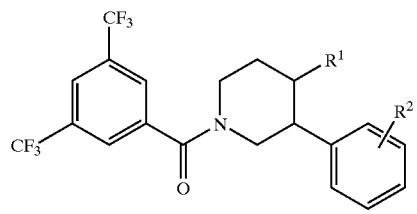

I-1 wherein
R$^1$ a) is unsubstituted phenyl, or phenyl substituted by one or two substituents, selected from the group R$^{1'}$, consisting of
halogen,
trifluoromethyl,
unsubstituted piperazinyl, or piperazinyl substituted by lower alkyl,
morpholinyl,
NH-phenyl,
pyrrolidinyl,
NH(CH$_2$)$_n$—O-lower alkyl,
NR$^a$R$^b$,
NH(CH$_2$)$_n$-cycloalkyl and,
NH(CH$_2$)$_n$—NR$^c$R$^d$, or is
- b) unsubstituted morpholinyl, or is
- c) unsubstituted piperazinyl or piperazinyl substituted by the group R$^{1'}$, which is selected from the group consisting of
  lower alkyl,
  cycloalkyl,
  C(O)-unsubstituted phenyl, or —C(O)-phenyl subsituted by trifluoromethyl,
  (CH$_2$)$_n$—C(O)—NR$^f$R$^g$,
  (CH$_2$)$_n$-cycloalkyl,
  (CH$_2$)$_n$-phenyl,
  C(O)-lower alkyl,
  C(O)—CF$_3$,
  C(O)-cycloalkyl,
  C(O)-morpholinyl,
  C(O)—O—(CH$_2$)$_n$—NR$^l$R$^m$ and
  (CH$_2$)$_n$—C(O)—N(R$^e$)-unsubstituted phenyl, or —(CH$_2$)$_n$—C(O)—N(R$^e$)-phenyl substituted by lower alkyl,
- d) -pyrazinyl, or is
- e) unsubstituted pyrrolidinyl, or pyrrolidinyl substituted by the group R$^{1'''}$, which is selected from
  hydroxy
  =O and,
  O—(CH$_2$)$_n$-cycloalkyl, or is
- f) unsubstituted piperidinyl or piperidinyl substituted by the group R$^{1''''}$, which is selected from
  hydroxy,
  O—(CH$_2$)$_n$-cycloalkyl,
  =O and
  halogen, or is
- g) thiomorpholinyl, 1-oxo-thiomorpholinyl or 1,1-dioxothiomorpholinyl;

R$^2$ is independently selected from the group consisting of hydrogen, halogen, lower alkyl, —NH—(CH$_2$)$_n$—O-lower alkyl, pyrrolidinyl and morpholinyl;

R, R$^a$, R$^b$, R$^c$, R$^d$, R$^e$, R$^f$, R$^g$, R$^l$, R$^m$ are independently selected from hydrogen or lower alkyl; and n is 1, 2, 3 or 4;

or a pharmaceutically acceptable acid addition salt thereof.

3. The compound according to claim 2 having the formula

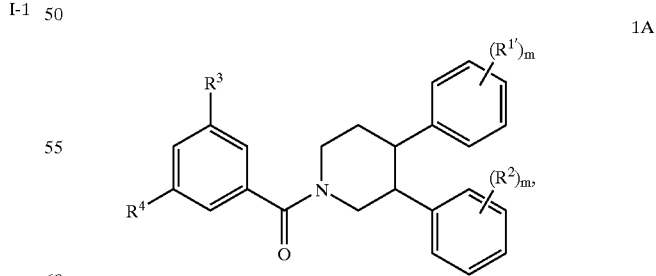

1A wherein m is 0, 1 or 2 and R$^{1'}$, R$^2$, R$^3$ and R$^4$ are described in claim 2.

4. The compound of formula 1A in accordance with claim 3, in which R$^{1'}$ is selected from the group consisting of hydrogen, bromo, morpholinyl, 4-methyl-piperazinyl and —NH(CH$_2$)$_2$OCH$_3$ and R$^2$.

5. The compound of formula 1A in accordance with claim 4, selected from the group consisting of
rac-cis-(3,5-bis-trifluoromethyl-phenyl)-[4-(4-morpholin-4-yl-phenyl)-3-phenyl-piperidin-1-yl]-methanone,
rac-cis-(3,5-bis-trifluoromethyl-phenyl)-{4-[4-(4-methyl-piperazin-1-yl)-phenyl]-3-phenyl-piperidin-1-yl}-methanone,
rac-cis-(3,5-bis-trifluoromethyl-phenyl)-[3-(4-chloro-phenyl)-4-phenyl-piperidin-1-yl]-methanone,
rac-cis-(3,5-bis-trifluoromethyl-phenyl)-[4-(3-bromo-phenyl)-3-phenyl-piperidin-1-yl]-methanone and
rac-cis-(3,5-bis-trifluoromethyl-phenyl)-{4-[4-(2-methoxy-ethylamino)-phenyl]-3-phenyl-piperidin-1-yl}-methanone.

6. A compound having the formula

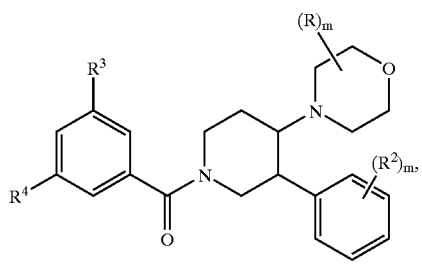

IB wherein R is lower alkyl, m is 0, 1 or 2, $R^2$, $R^3$ and $R^4$ have the significances given in claim 1.

7. The compound of formula 1B in accordance with claim 6, wherein $R^2$ is selected from the group consisting of hydrogen, fluoro and chloro.

8. The compound of formula 1B in accordance with claim 7, wherein the compound is selected from the group consisting of
rac-cis-(3,5-bis-trifluoromethyl-phenyl)-[3-(4-chloro-phenyl)-4-morpholin-4-yl-piperidin-1-yl]-methanone,
rac-cis-(3,5-bis-trifluoromethyl-phenyl)-(4-morpholin-4-yl-3-phenyl-piperidin-1-yl)-methanone,
rac-cis-(3,5-bis-trifluoromethyl-phenyl)-[3-(4-fluoro-phenyl)-4-morpholin-4-yl-piperidin-1-yl]-methanone and
Rac-cis-(3,5-bis-trifluoromethyl-phenyl)-[3'-(4-chloro-phenyl)-4-morpholin-4-yl-[1,4']bipiperidinyl-1'-yl]-methanone.

9. A compound having the formula

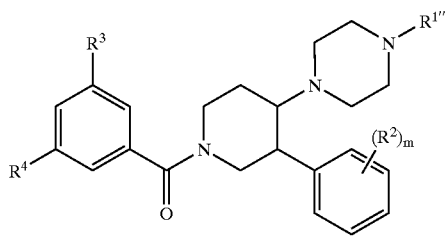

IC wherein m is 0, 1 or 2, $R^{1''}$, $R^2$, $R^3$ and $R^4$ have the significances given in claim 1.

10. The compound of formula IC in accordance with claim 9, wherein $R^{1''}$ is selected from the group consisting of hydrogen, methyl, —C(O)CF$_3$, —(CH$_2$)$_2$OH, —CH$_2$C(O)N(CH$_3$)$_2$, CH$_2$-cyclopropyl, benzyl, —C(O)-cyclopropyl, —C(O)-morpholinyl, pyrazinyl, cyclopropyl —CH$_2$CONHC$_6$H$_3$(CH$_3$)$_2$, —CH$_2$CONHC$_6$H$_4$F and —C(O)CH$_2$-phenyl, and R$_2$ is selected from the group consisting of hydrogen, methyl, chloro and fluoro.

11. The compound of formula 1C in accordance with claim 10, wherein the compound is selected from the group consisting of
rac-cis-(3,5-bis-trifluoromethyl-phenyl)-[4-(4-methyl-piperazin-1-yl), -3-phenyl-piperidin-1-yl]-methanone,
rac-cis-(3,5-bis-trifluoromethyl-phenyl)-(3-phenyl-4-piperazin-1-yl-piperidin-1-yl)-methanone,
rac-cis-2{4-[1-(3,5-bis-trifluoromethyl-benzoyl)-3-phenyl-piperidin-4-yl]-piperazin-1-yl}-N,N-dimethyl-acetamide,
rac-cis-(3,5-bis-trifluoromethyl-phenyl)-[4-(4-cyclopropylmethyl-piperazin-1-yl)-3-phenyl-piperidin-1-yl]-methanone,
rac-cis-[4-(4-benzyl-piperazin-1-yl)-3-phenyl-piperidin-1-yl]-(3,5-bis-trifluoromethyl-phenyl)-methanone,
rac-cis-(3,5-bis-trifluoromethyl-phenyl)-[4-(4-cyclopropanecarbonyl-piperazin-1-yl)-3-phenyl-piperidin-1-yl]-methanone,
rac-cis-{4-[1-(3,5-bis-trifluoromethyl-benzoyl)-3-phenyl-piperidin-4-yl]-piperazin-1-yl}-morpholin-4-yl-methanone,
rac-cis-(3,5-bis-trifluoromethyl-phenyl)-[4-(4-cyclopropyl-piperazin-1-yl)-3-phenyl-piperidin-1-yl]-methanone,
rac-cis-(3,5-bis-trifluoromethyl-phenyl)-[3-(4-fluoro-phenyl)-4-(4-methyl-piperazin-1-yl)-piperidin-1-yl]-methanone,
rac-cis-2-{4-[1-(3,5-bis-trifluoromethyl-benzoyl)-3-phenyl-piperidin-4-yl]-piperazin-1-yl}-N-(2,6-dimethyl-phenyl)-acetamide,
rac-cis-(3,5-bis-trifluoromethyl-phenyl)-[3-phenyl-4-(2,3,5,6-tetrahydro-[1,2']bipyrazinyl-4-yl)-piperidin-1-yl]-methanone,
(+)-(3,5-bis-trifluoromethyl-phenyl)-[4-(4-cyclopropanecarbonyl-piperazin-1-yl)-3-phenyl-piperidin-1-yl]-methanone,
Rac-cis-2-{4-[1-(3,5-bis-trifluoromethyl-benzoyl)-3-phenyl-piperidin-4-yl]-piperazin-1-yl}-N-(4-fluoro-phenyl)-acetamide,
Rac-cis-1-{4-[1-(3,5-bis-trifluoromethyl-benzoyl)-3-phenyl-piperidin-4-yl]-piperazin-1-yl}-2-phenyl-ethanone,
Rac-cis-(3,5-bis-trifluoromethyl-phenyl)-[3-(4-fluoro-phenyl)-4-piperazin-1-yl-piperidin-1-yl]-methanone,
Rac-cis-(3,5-bis-trifluoromethyl-phenyl)-[4-(4-cyclopropylmethyl-piperazin-1-yl)-3-(4-fluoro-phenyl)-piperidin-1-yl]-methanone,
(−)-(3,5-bis-trifluoromethyl-phenyl)-[3-(4-fluoro-phenyl)-4-(4-methyl-piperazin-1-yl)-piperidin-1-yl]-methanone,
(−)-(3,5-bis-trifluoromethyl-phenyl)-[3-phenyl-4-(4-methyl-piperazin-1-yl)-piperidin-1-yl]-methanone,
(−)-4-(3,5-bis-trifluoromethyl-phenyl)-[4-(4-cyclopropylmethyl-piperazin-1-yl)-3-p-tolyl-piperidin-1-yl]-methanone,
(−)-(3,5-bis-trifluoromethyl-phenyl)-[4-(4-cyclopropanecarbonyl-piperazin-1-yl)-3-p-tolyl-piperidin-1-yl]-methanone,
(−)-(3,5-bis-trifluoromethyl-phenyl)-{4-[4-(morpholine-4-carbonyl)-piperazin-1-yl]-3-p-tolyl-piperidin-1-yl}-methanone,
Rac-cis-1-{4-[1-(3,5-bis-trifluoromethyl-benzoyl)-3-(4-chloro-phenyl)-piperidin-4-yl]-piperazin-1-yl}-2,2,2-trifluoro-ethanone,
(−)-1-{4-[1-(3,5-bis-trifluoromethyl-benzoyl)-3-(4-chloro-phenyl)-piperidin-4-yl-piperazin-1-yl}-2,2,2-trifluoro-ethanone,
(−)-(3,5-bis-trifluoromethyl-phenyl)-[4-(4-cyclopropyl-piperazin-1-yl)-3-p-tolyl-piperidin-1-yl]-methanone,
(−)-(3,5-bis-trifluoromethyl-phenyl)-[4-(4-methyl-piperazin-1-yl)-3-p-tolyl-piperidin-1-yl]-methanone, (-)-(3,5-bis-trifluoromethyl-phenyl)-[3-(4-chloro-phenyl)-4-(4-cyclopropylmethyl-piperazin-1-yl)-piperidin-1-yl]-methanone, (-)-(3,5-bis-trifluoromethyl-phenyl)-[4-(4-cyclopropylmethyl-piperazin-1-yl)-3-phenyl-piperidin-1-yl]-methanone, (-)-(3,5-bis-trifluoromethyl-phenyl)-{4-[4-(2-hydroxy-ethyl)-piperazin-1-yl]-3-phenyl-piperidin-1-yl}-methanone and (-)-(3,5-bis-trifluoromethyl-phenyl)-[4-(4-cyclopropyl-piperazin-1-yl)-3-phenyl-piperidin-1-yl]-methanone.

12. A compound having the formula

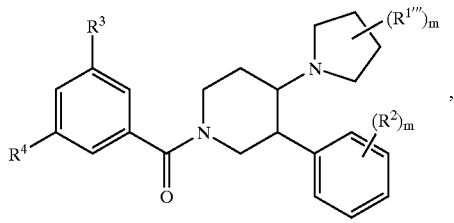

ID wherein m is 0, 1 or 2, $R^{1'''}$, $R^2$, $R^3$ and $R^4$ have the significances given in claim 1.

13. The compounds of formula ID in accordance with claim 12, wherein $R^{1'''}$ is selected from the group consisting of hydrogen, hydroxy, amino, —OCH$_2$-cyclopropyl and =O and $R^2$ is selected from the group consisting of hydrogen, chloro and fluoro.

14. The compound of formula 1D in accordance with claim 13, wherein the compound is selected from the group consisting of (3R,3'R,4R)- and (3S,3'R,4S)-(3,5-bis-trifluoromethyl-phenyl)-[4-(3'-hydroxy-pyrrolidin-1'-yl)-3-phenyl-piperidin-1-yl]-methanone, (3R,3'R,4R)- and (3S,3'R,4S)-(3,5-bis-trifluoromethyl-phenyl)-[4-(3-cyclopropylmethoxy-pyrrolidin-1-yl)-3-phenyl-piperidin-1-yl]-methanone, rac-cis-1-[1-(3,5-bis-trifluoromethyl-benzoyl)-3-phenyl-piperidin-4-yl]-pyrrolidin-3-one, (-)-(3,5-bis-trifluoromethyl-phenyl)-[3-(4-chloro-phenyl)-4-pyrrolidin-1-yl-piperidin-1-yl]-methanone and (3RS,3'RS,4SR)- and (3RS,3'SR,4SR)-[4-(3-Amino-pyrrolidin-1-yl)-3-(4-fluoro-phenyl)-piperidin-1-yl]-(3,5-bis-trifluoromethyl-phenyl)-methanone.

15. A compound having the formula

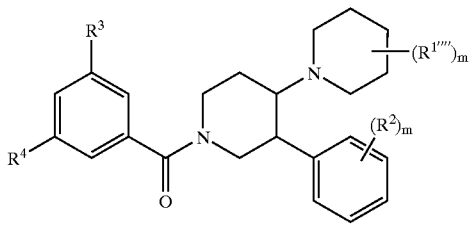

IE wherein m is 0, 1 or 2, $R^{1''''}$, $R^2$, $R^3$ and $R^4$ have the significances given in claim 1.

16. The compound of formula IE in accordance with claim 15, wherein $R^{1''''}$ is selected from the group consisting of fluoro, hydroxy, —NHC(O)-cyclopropyl, —NHC(O)CH$_2$-phenyl, —NH-cyclopropyl, —N(CH$_2$)$_2$, —OCH$_2$-cyclopropyl and =O and wherein $R^2$ is selected from the group consisint of hydrogen, chloro and fluoro.

17. The compound of formula 1E in accordance with claim 16, wherein the compound is selected from the group consisting of rac-cis-(3,5-bis-trifluoromethyl-phenyl)-(4,4-difluoro-3'-phenyl-[1,4']bipiperidinyl-1'-yl)-methanone, rac-cis-(3,5-bis-trifluoromethyl-phenyl)-[3'-(4-fluoro-phenyl)-3-hydroxy-1,4']bipiperidinyl-1'-yl]-methanone, rac-cis-(3,5-bis-trifluoromethyl-phenyl)-(4-hydroxy-3'-phenyl-1,4']bipiperidinyl-1'-yl)-methanone, rac-cis-(3,5-bis-trifluoromethyl-phenyl)-(4-cyclopropylmethoxy-3'-phenyl-[1,4']bipiperidinyl-1'-yl)-methanone, rac-cis-1'-(3,5-bis-trifluoromethyl-benzoyl)-3'-phenyl-[1,4']bipiperidinyl-4-one, Rac-cis-(3,5-bis-trifluoromethyl-phenyl)-[3'-(4-chloro-phenyl)-4-hydroxy-[1,4']bipiperidinyl-1'-yl]-methanone, Rac-cis-(3,5-bis-trifluoromethyl-phenyl)-[3'-(4-chloro-phenyl)-4-cyclopropylmethoxy-[1,4']bipiperidinyl-1'-yl]-methanone, (3RS,3'RS,4SR)- and (3RS,3'SR,4SR)-cyclopropanecarboxylic acid [1'-(3,5-bis-trifluoromethyl-benzoyl)-3'-(4-fluoro-phenyl)-[1,4']bipiperidinyl-3-yl]-amide, (3RS,3'RS,4SR)- and (3RS,3'SR,4SR)-N-[1'-(3,5-bis-trifluoromethyl-benzoyl)-3'-(4-fluoro-phenyl)-[1,4']bipiperidinyl-3-yl]-2-phenyl-acetamide, Rac-cis-(3,5-bis-trifluoromethyl-phenyl)-[3'-(4-chloro-phenyl)-4-dimethylamino-[1,4']bipiperidinyl-1'-yl]-methanone and Rac-cis-(3,5-bis-trifluoromethyl-phenyl)-[3'-(4-chloro-phenyl)-4-cyclopropylamino-[1,4']bipiperidinyl-1'-yl]-methanone.

18. A compound having the formula

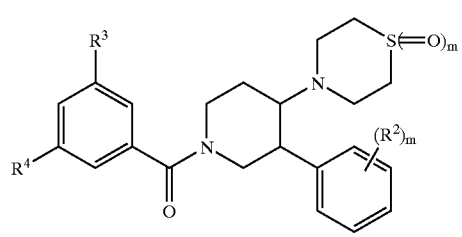

1F wherein $R^2$, $R^3$ and $R^4$ are described in claim 1 and m is 0, 1 or 2.

19. The compound of formula IF in accordance with claim 18, wherein m is 0, 1 or 2 and $R^2$ is hydrogen.

20. The compound of formula 1F in accordance with claim 19, wherein the compound is selected from the group consisting of rac-cis-(3,5-bis-trifluoromethyl-phenyl)-(3-phenyl-4-thiomorpholin-4-yl-piperidin-1-yl)-methanone, rac-cis-(3,5-bis-trifluoromethyl-phenyl)-[4-(1-oxo-1l4-thiomorpholin-4-yl)-3-phenyl-piperidin-1-yl]-methanone and rac-cis-(3,5-bis-trifluoromethyl-phenyl)-[4-(1,1-dioxo-1l6-thiomorpholin-4-yl)-3-phenyl-piperidin-1-yl]-methanone.

21. A pharmaceutical composition comprising a pharmaceutically effective amount of a compound of formula 1 or a pharmaceutically acceptable salt thereof and a pharmaceutically acceptable excipient.

22. A method of treating a disease modulated by an antagonist of the neurokinin 1 receptor comprising administering a pharmacuetically effective amount of a compound of formula 1 or a pharmaceutically acceptable salt thereof to a patient in need of such treatment.

23. A method of treating depression comprising administering a pharmaceutically effective amount of a compound of formula 1 or a pharmaceutically acceptable salt thereof to a patient in need of such treatment.

24. A method of treating emesis comprising administering a pharmaceutically effective amount of a compound of formula 1 or a pharmaceutically acceptable salt thereof to a patient in need of such treatment.

25. A process for preparing a compound of formula 1, which process comprises a) reacting a compound of formula

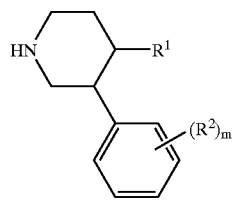

II with a compound of formula

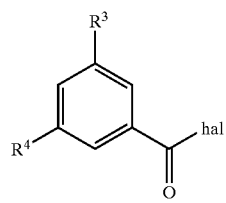

III forming a compound of formula

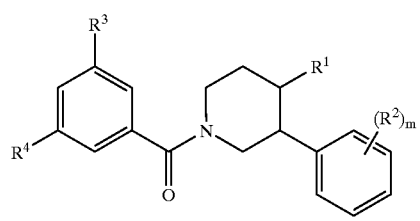

I wherein R¹ is unsubstituted phenyl or phenyl substituted by halogen, R², R³ and R⁴ have the significances given in claim 1, hal is halogen and m is 0, 1 or 2, or b) reacting a compound of formula

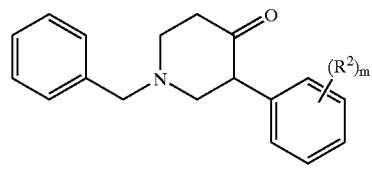

IV with a compound selected from the group consisting of formulae

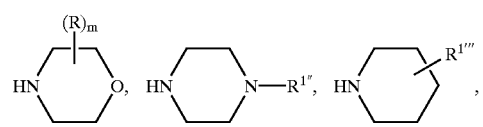

-continued

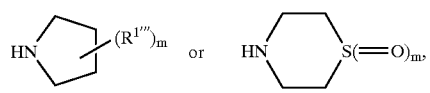

debenzylating, and then acylating with a compound of formula III forming a compound of formulae

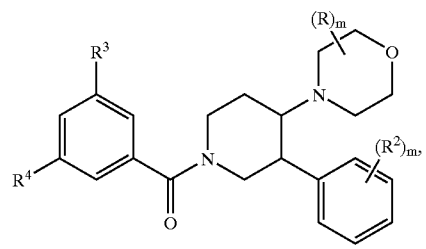

IB wherein R, R², R³, R⁴ and m have the significances given in claim 1, or

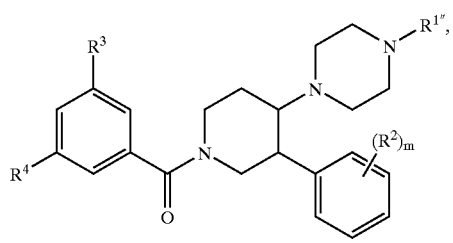

IC wherein R¹″, R², R³, R⁴ and m have the significances given in claim 1, or

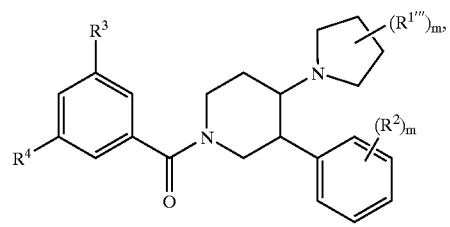

ID wherein R¹‴, R², R³, R⁴ and m have the significances given in claim 1, or

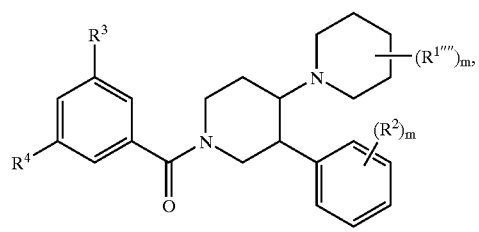

IE wherein R¹″″, R², R³, R⁴ and m have the significances given in claim 1, or

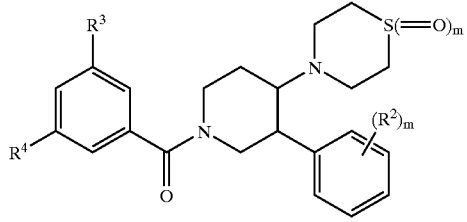
IF wherein $R^2$, $R^3$, $R^4$ and m have the significances given in claim 1, or c) aminating a compound of formula

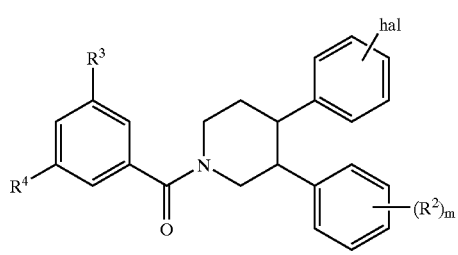
V with an amine derivative of formula $R^1H$     VI forming a compound of formula

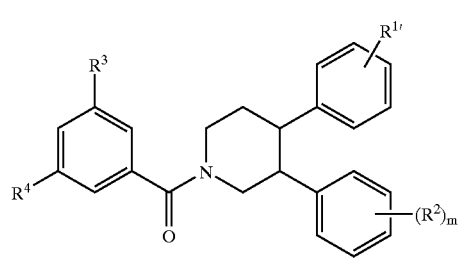
IA1 wherein $R^{1'}$ is unsubstituted piperazinyl, or piperazinyl substituted by a substituent selected from the group consisting of lower alkyl, morpholinyl, —NH-phenyl, pyrrolidinyl, —NH$(CH_2)_n$—O-lower alkyl, —NR$_2$, —NH $(CH_2)_n$-cycloalkyl and —NH$(CH_2)_n$-NR$_2$, and wherein the definitions of $R^2$, $R^3$ and $R^4$ are given in claim 1, or d) reacting a compound of formula

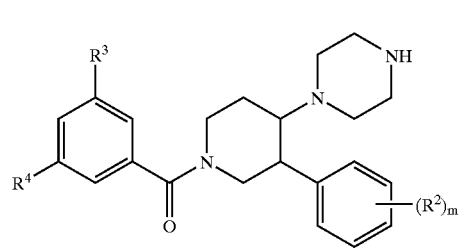
IC1 with a compound of formula $R^{1''}hal$     VII forming a compound of formula

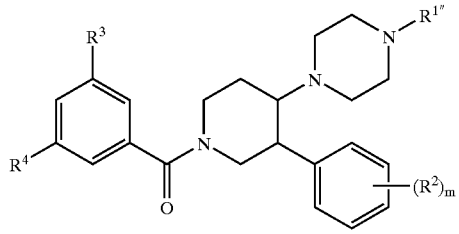
IC wherein the definitions of $R^{1''}$, $R^2$, $R^3$, $R^4$ and m are given in claim 1, or e) oxidizing a compound of formula

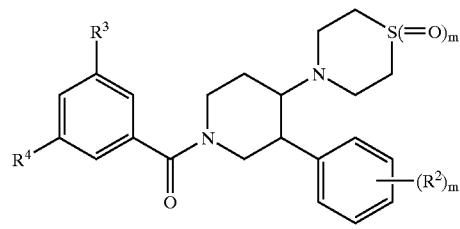
IF1 with Oxone® forming a compound of formula

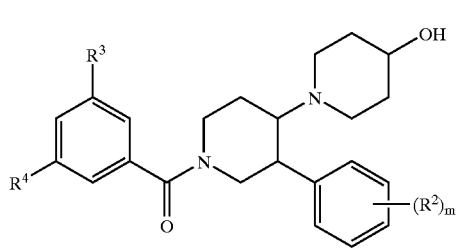
IF wherein m is 1 or 2 and $R^2$, $R^3$ and $R^4$ are described in claim 1, or f) alkylating a compound of formula

IE1 with a compound of formula

R⁵hal                    VIII forming a compound of formula

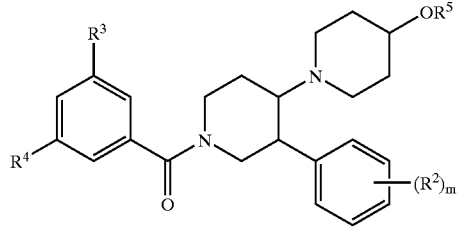  IE2 wherein R⁵ is —(CH₂)$_n$-cycloalkyl, and R², R³, R⁴ and m are described in claim 1, or or g) oxidizing a compound of formula

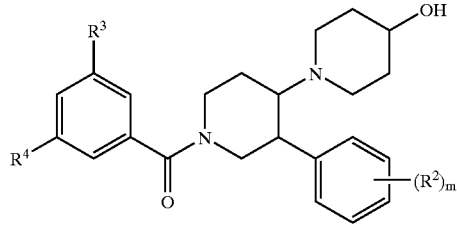  IE1 forming a compound of formula

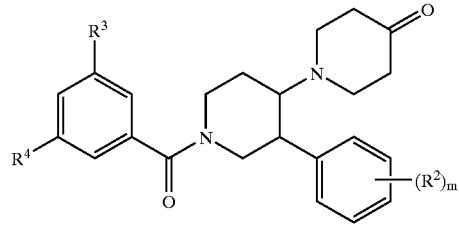  IE3 wherein R², R³, R⁴ and m are described in claim 1, or
h) halogenating a compound of formula

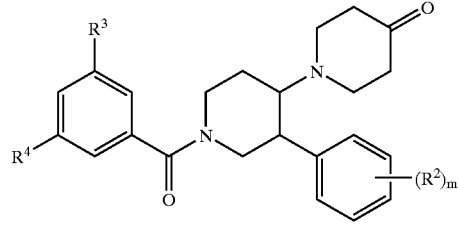  IE3 forming a compound of formula

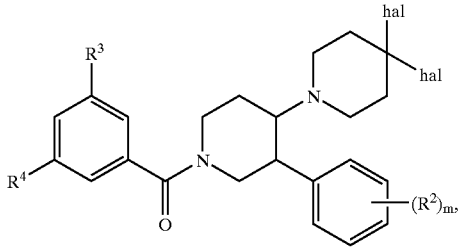  IE4 and
converting the compound obtained into a pharmaceutically acceptable acid addition salt.

* * * * *